United States Patent
Chevalier et al.

(10) Patent No.: US 9,434,800 B2
(45) Date of Patent: Sep. 6, 2016

(54) METHOD OF EMBOLIZATION USING A RADIOPAQUE, NON-BIODEGRADABLE, WATER-INSOLUBLE IODINATED BENZYL ETHER OF POLY(VINYL ALCOHOL)

(71) Applicants: Antia Therapeutics S.A., Bern (CH); Université Claude Bernard Lyon 1 (UCBL), Villeurbanne (FR); Centre National de la Recherche Scientifique (CNRS), Paris (FR)

(72) Inventors: Yves Chevalier, Vernaison (FR); Géraldine Agusti, Villeurbanne (FR); Coralie Nyffenegger, Fontenay-aux-Roses (FR); Eric Doelker, Conches (CH); Olivier Jordan, Prangins (CH); Gert Andersen, Copenhague (DK)

(73) Assignees: ANTIA THERAPEUTICS S.A., Bern (CH); UNIVERSITE CLAUDE BERNARD LYON 1, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/794,134

(22) Filed: Jul. 8, 2015

(65) Prior Publication Data
US 2015/0335779 A1 Nov. 26, 2015

Related U.S. Application Data

(62) Division of application No. 13/578,106, filed as application No. PCT/EP2011/053536 on Mar. 9, 2011, now Pat. No. 9,115,230.

(30) Foreign Application Priority Data

Mar. 10, 2010 (EP) .................................. 10156039

(51) Int. Cl.
| | | |
|---|---|---|
| A61L 24/04 | (2006.01) |
| A61L 24/06 | (2006.01) |
| C08F 116/06 | (2006.01) |
| A61K 49/04 | (2006.01) |
| C08F 8/18 | (2006.01) |

(52) U.S. Cl.
CPC ......... *C08F 116/06* (2013.01); *A61K 49/0442* (2013.01); *A61L 24/043* (2013.01); *A61L 24/06* (2013.01); *C08F 8/18* (2013.01); *A61L 2400/06* (2013.01); *A61L 2430/36* (2013.01)

(58) Field of Classification Search
None
See application file for complete search history.

(56) References Cited

U.S. PATENT DOCUMENTS

| | | |
|---|---|---|
| 4,406,878 A | 9/1983 | DeBoer |
| 2005/0265923 A1 | 12/2005 | Toner et al. |

FOREIGN PATENT DOCUMENTS

| | | |
|---|---|---|
| CN | 101513542 | 8/2009 |
| WO | WO 99/12577 A1 | 3/1999 |
| WO | WO 01/22948 A1 | 4/2001 |

OTHER PUBLICATIONS

International Search Report for International Application No. PCT/EP2011/053536 dated Mar. 30, 2011.
Database WPI, Week 200966, Thomson Scientific, London, GB; AN 2009-N34393 XP002630295, and CN 101 513 542 A (Shandong Dazheng Medical Appliance Co Lt) Aug. 26, 2009, 31 pages.
Kim, E. H. et al., "Biomedical applications of superparamagnetic iron oxide nanoparticles encapsulated within chitosan," *Journal of Alloys and Compounds* 434-435 (2007), pp. 633-636.
Mawad, D. et al., "Elaboration of radiopaque iodinated nonparticles for in situ control of local drug delivery," *Biomaterials* 30 (2009), pp. 5667-5674.
Mawad, D. et al., "Synthesis and Characterization of Radiopaque Iodine-containing Degradable PVA Hydrogel," *Biomacromolecules*, vol. 9, No. 1 (2008), pp. 263-268.
Pan, Z. et al., book "Water-soluble polymer product Application Technology," Chemical Industry Press, Feb. 2006, 1st ed., front reference of book (2 sheets) and p. 4.

*Primary Examiner* — Mina Haghighatian
*Assistant Examiner* — Luke Karpinski
(74) *Attorney, Agent, or Firm* — Brinks Gilson & Lione; G. Peter Nichols

(57) ABSTRACT

A method of embolizing an area of treatment includes providing a composition that includes a radiopaque, non-biodegradable, water-insoluble iodinated benzyl ether of poly(vinyl alcohol) consisting of a poly(vinyl alcohol) (PVA) having covalently grafted thereon iodinated benzyl groups comprising from 1 to 4 iodine atoms per benzyl group as the only substituents wherein a grafted repeating unit has formula (I)

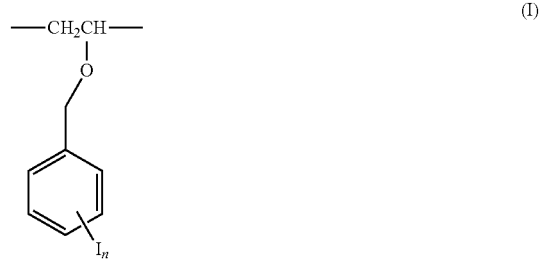

wherein n is from 1 to 4: and introducing the composition into the area of treatment.

14 Claims, 8 Drawing Sheets

METHOD OF EMBOLIZATION USING A RADIOPAQUE, NON-BIODEGRADABLE, WATER-INSOLUBLE IODINATED BENZYL ETHER OF POLYL(VINYL ALCOHOL)

This application is a divisional of U.S. application Ser. No. 13/578,106, Filed Aug. 9, 2012, which claims the benefit under 35 U.S.C. §371 of International Application No. PCT/EP2011/053536, having an International Filing Date of Mar. 9, 2011, which claims priority to EP Application No. 10156039.9, filed Mar. 10, 2010; the entire contents of each are incorporated herein by reference in their entirety.

FIELD OF THE INVENTION

The present invention relates to radiopaque, non-biodegradable, water-insoluble iodinated polymers, and more particularly to radiopaque, non-biodegradable, water-insoluble, iodinated benzyl ethers of poly(vinyl alcohol), to their use as embolizing agents, to a process for producing thereof, to injectable embolizing compositions containing thereof and the uses thereof, to coating compositions containing thereof and to micro- and nanoparticles made thereof.

BACKGROUND OF THE INVENTION

The embolization of a blood vessel is important in preventing/controlling bleeding (e.g., organ bleeding, gastrointestinal bleeding, vascular bleeding, bleeding associated with an aneurysm) or to ablate diseased tissue (e.g., tumors, etc.) by cutting off its blood supply.

Endovascular embolization of blood vessels is known to be conducted as alternative to surgical interventions for a variety of purposes including the endovascular treatment of tumors, the treatment of lesions such as aneurysms, arteriovenous malformations, arteriovenous fistula, uncontrolled bleeding and the like.

Endovascular embolization of blood vessels is accomplished via catheter techniques which permit the selective placement of the catheter at the vascular site to be embolized.

Recent techniques proposed to embolize blood vessels by using injectable embolizing compositions including polymeric materials as embolizing agents.

The use of embolizing compositions in the treatment of aneurysms or arteriovenous malformations (AVMs) is advantageous since the polymeric materials fill the inside of the aneurysms or AVM and solidify in the shape of the aneurysm or AVM, therefore the aneurysm or AVM will be completely excluded from the blood circulation.

It is also known that injectable embolizing compositions containing polymeric materials as embolizing agents may be used for treating tumors by direct puncture. In such a case, the embolizing composition is directly injected into the tumoral tissue or the vascular bed surrounding the tumor via a needle technology.

Known polymeric materials employed in embolizing compositions include for example those wherein a preformed polymer in situ precipitates from a carrier solution at the vascular site or into the tumor.

In embolizing compositions, the preformed polymer must be selected to be capable of rapid precipitation to form a well defined cohesive solid or semi-solid mass, space-filling material upon contact with blood or any other body aqueous environment in a tissue.

Additionally, these compositions should be sterile, stable, biocompatible, and further highly radiopaque to allow for an efficient imaging using current radiology techniques.

This last property is necessary in order to visualize the embolizing composition during injection, deposition into the vascular site, and clinical follow-up.

A number of documents disclose liquid formulations intended for the embolization of blood vessels and containing a water-insoluble, organo-soluble biocompatible preformed polymer dissolved in a biocompatible water-miscible organic solvent, and a solid water-insoluble biocompatible radiopaque contrast agent such as tantalum, tantalum oxide, tungsten, bismuth trioxide and barium sulfate.

These known radiopaque embolizing compositions, precipitating upon contact with blood, are simple physical mixtures of a preformed polymer dissolved in a water-miscible organic solvent and a conventional radiopaque contrast agent.

U.S. Pat. No. 5,580,568 discloses compositions suitable for use in embolizing blood vessels which comprise a cellulose diacetate polymer, a biocompatible solvent such as DMSO and a water insoluble contrast agent such as tantalum, tantalum oxide and barium sulfate.

U.S. Pat. No. 5,851,508 discloses compositions suitable for use in embolizing blood vessels which comprises an ethylene vinyl alcohol copolymer, a biocompatible solvent such as DMSO and a water insoluble contrast agent such as tantalum, tantalum oxide and barium sulfate.

U.S. Pat. No. 5,695,480 discloses compositions for use in embolizing blood vessels which comprise a biocompatible polymer selected from cellulose acetates, cellulose acetate propionates, cellulose acetate butyrates, ethylene vinyl alcohol copolymers, hydrogels, polyacrylonitrile, polyvinylacetate, nitrocellulose, copolymers of urethane/carbonate, copolymers of styrene/maleic acid and mixtures thereof, a biocompatible solvent such as DMSO, ethanol and acetone, and a contrast agent such as tantalum, tantalum oxide, tungsten and barium sulfate.

However, in these formulations, the radiopaque contrast agent is suspended in the polymer solution, so that these embolizing compositions are heterogeneous dispersions.

Thus, permanent radiopacity may not be ensured with these compositions because chemical incorporation of the contrast agent into the polymer structure is not achieved and sedimentation of the contrast agent during catheterization or slow release with time in the surrounding areas could occur, which would be a major drawback for clinical follow-up and could lead to serious toxic-effects.

A well-known commercially available formulation of this type is ONYX™, a mixture of ethylene-vinyl alcohol copolymer (EVOH) dissolved in DMSO, with micronized tantalum powder in the liquid polymer/DMSO mixture to provide fluoroscopic visualization.

ONYX™ is delivered through a microcatheter to the target lesion under fluoroscopic control.

Upon contact with body fluid (i.e. blood), the solvent (DMSO) rapidly diffuses away causing in-situ precipitation of the polymer in the presence of the radiopaque contrast agent, thus forming a radiopaque polymeric implant.

ONYX™ is available in a range of liquid viscosities intended to have delivery and precipitation characteristics optimized for the type of lesion being treated.

However, these formulations have the following drawbacks.

These formulations need careful preparation before use, which is time consuming and may lead to application errors.

Further, since the radiopaque contrast agent is suspended in the polymer solution, homogeneous radiopacity may not be ensured with respect to possible sedimentation during embolization. The radiopaque contrast agent also limits non-invasive follow-up imaging by CT scanning because of beam-hardening artifacts. Furthermore, the entrapment of the metallic radiopaque contrast agent is not ensured so that phase separation may occur.

As a consequence, the radiopaque contrast agent does not reflect the position of the polymer and implant visibility may change during radiological imaging follow-up studies. Released metallic radiopaque contrast agents are potentially toxic.

To overcome the drawbacks of formulations containing a radiopaque agent in suspension in the polymer solution, some of the present inventors have focused on the need to provide an intrinsically radiopaque polymer for use as embolizing agent in liquid embolizing compositions.

For this purpose, they have synthesized a iodinated poly(vinyl alcohol) (I-PVA) by grafting iodobenzoyl chloride to poly(vinyl alcohol) via ester linkages and tested such an I-PVA polymer.

The results obtained when such an I-PVA is used in liquid embolizing compositions were reported in a number of publications (see O. Jordan et al., 19th European Conference on Biomaterials, 2005, Sorrento, Italia, *"Novel organic vehicles for the embolization of vascular malformations and intracranial aneurysms"*; O. Jordan et al., Transactions of the 7th World Biomaterials Congress, Sydney, Australia, 706, 2004, *"Novel Radiopaque Polymer for Interventional Radiology"*; O. Jordan et al., American Society of Neuroradiology 42nd annual meeting, Seattle, Jun. 5-11, 2004, *"Liquid Embolization of Experimental Wide-Necked Aneurysms with Polyvinyl Alcohol Polymer: A New, Nonadhesive, Iodine-Containing Liquid Embolic Agent"*; O. Dudeck, O. Jordan et al., Am. J. Neuroradiol., 27:1900-1906, 2006, *"Organic solvents as vehicles for precipitating liquid embolics"*; O. Dudeck, O. Jordan et al.; Am. J. Neuroradiol., 27: 1849-55, October 2006, *"Embolization of Experimental Wide-Necked Aneurysm with Iodine-Containing Polyvinyl Alcohol Solubilized in a Low-Angiotoxicity Solvent"*; O. Dudeck, O. Jordan et al., J. Neurosurg. 104: 290-297, February 2006, *"Intrinsically radiopaque iodine-containing polyvinyl alcohol as a liquid embolic agent: evaluation in experimental wide-necked aneurysms"*) without identifying the I-PVA used.

However, this I-PVA lacks stability with respect to hydrolysis, and when used as embolizing agent, undergoes partial degradation leading to potentially toxic degradation products in the body over time.

Moreover, since the embolic mass is expected to stand for a long duration, sustainable attachment of the iodinated markers is required.

Therefore, the present inventors have focused their research on the need to provide a new iodinated poly(vinyl alcohol) which has an improved stability, and have surprisingly found a new iodinated poly(vinyl alcohol) which has not only an improved stability with respect to hydrolysis, but which is also expected to provide liquid embolizing compositions having higher concentration of embolizing agent, and therefore lower volume of organic solvent due to its unexpected low viscosity in solution, and have thus achieved the present invention.

SUMMARY OF THE INVENTION

According to a first aspect, the present invention provides a radiopaque, non-biodegradable, water-insoluble iodinated benzyl ether of poly(vinyl alcohol) (iodo-benzylether-PVA) consisting of a poly(vinyl alcohol) having covalently grafted thereon iodinated benzyl groups comprising 1-4 iodine atoms per benzyl group.

According to a second aspect, the present invention provides a process for preparing the iodo-benzylether-PVA of the present invention, said process comprising reacting a 0-100% hydrolyzed poly(vinyl alcohol) as a starting PVA with a iodinated benzyl derivative comprising 1-4 iodine atoms per benzyl group in a polar aprotic solvent in the presence of a base in anhydrous conditions.

According to a third aspect, the present invention provides a use of the iodo-benzylether-PVA of the present invention as an embolic agent in an injectable embolizing composition. In this regard, the iodo-benzylether-PVA of the present invention can be introduced into the area of treatment.

According to a fourth aspect, the present invention provides an injectable embolizing composition comprising the iodo-benzylether-PVA of the present invention and a water-miscible, biocompatible solvent solubilizing the iodo-benzylether-PVA, wherein the concentration of the iodo-benzylether-PVA in the composition is selected in the range of 5-65 w/w % so that the composition is capable of forming a cohesive mass upon contact with a body fluid by precipitation of the iodo-benzylether-PVA.

According to a fifth aspect, the present invention provides a use of the injectable embolizing composition of the present invention for forming in-situ a cohesive mass in a blood vessel such as arteriovenous malformation (AVMs) or vascular aneurysms.

According to a sixth aspect, the present invention provides a use of the injectable embolizing composition of the present invention for forming in-situ a cohesive mass into a tumor.

According to a seventh aspect, the present invention provides a use of the injectable embolizing composition of the present invention for forming in-situ a semi-solid implant into a tumor for treating the tumor by hyperthermia.

According to a eighth aspect, the present invention provides a use of the injectable embolizing composition of the present invention for forming in-situ a semi-solid implant for treating urinary incontinence.

According to a ninth aspect, the present invention provides a coating composition for forming a coating on a medical device comprising the iodo-benzylether-PVA of the present invention and a solvent solubilizing the iodo-benzylether-PVA, wherein the concentration of the iodo-benzylether-PVA in the composition is selected in the range of 5-65 w/w % so that the composition is capable of forming a radiopaque coating after application on a medical device and solvent evaporation.

According to a tenth aspect, the present invention provides particles, selected from microparticles and nanoparticles, formed of the iodo-benzylether-PVA of the present invention.

DETAILED DESCRIPTION OF THE PRESENT INVENTION

Figure 1:
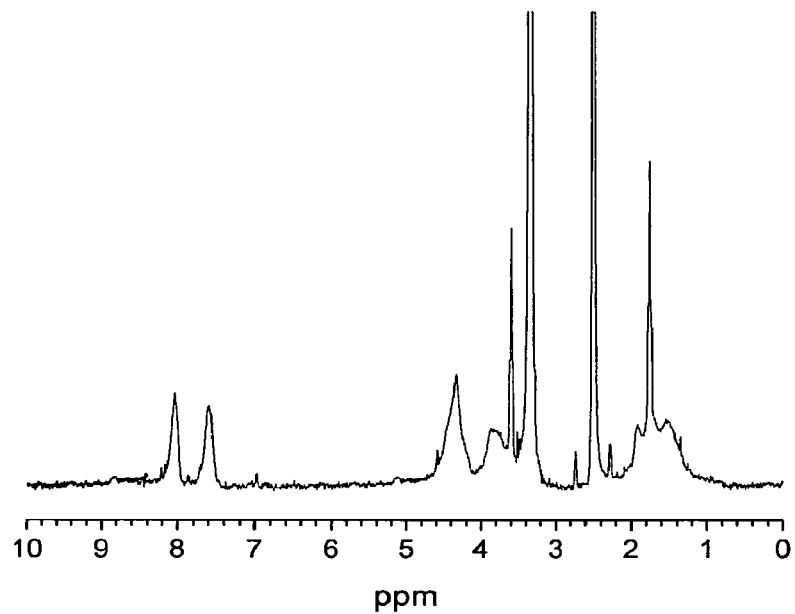
FIG. 1 shows the $^1$H-NMR spectrum of 2,3,5-triiodobenzylether of poly(vinyl alcohol) of the present invention prepared according to Example 1.

It is to be noted that in the present description and claims, the iodinated benzyl ether of poly(vinyl alcohol) of the present invention will be designed as "iodo-benzylether-PVA of the present invention".

The iodo-benzylether-PVA of the present invention is a radiopaque, non-biodegradable, water-insoluble iodinated benzyl ether of poly(vinyl alcohol) consisting of a poly(vinyl alcohol) having covalently grafted thereon iodinated benzyl groups comprising 1-4 iodine atoms per benzyl group via ether linkages.

The degree of substitution (DS) of the iodo-benzylether-PVA of the present invention is not particularly limited.

However, in order to provide an appropriate radiopacity to the iodo-benzylether-PVA of the present invention, the degree of substitution (DS) is preferably of at least 0.2.

In a preferred embodiment, the degree of substitution is of at least 0.4, and more preferably of at least 0.5.

The degree of substitution (DS) is defined as $$DS = x/(x+y)$$

wherein
x represents the number of grafted repeating units, and
x+y represents the total number of repeating units (grafted repeating units and non-grafted repeating units),
as calculated from the integration of the NMR lines of the iodo-benzylether-PVA of the present invention.

For clarifying what is meant by grafted and non-grafted repeating units in the iodo-benzylether-PVA of the present invention, a grafted repeating unit may be represented by

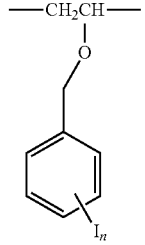

wherein n represents the number of iodine atoms on benzyl group, and a non-grafted repeating unit may be represented by

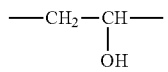

The iodine content (% I) of the iodo-benzylether-PVA of the present invention is not particularly limited, but should preferably be of at least 20% (w/w) for making it sufficiently radiopaque.

In a preferred embodiment of the present invention, the iodo-benzylether-PVA has a iodine content of at least 40% (w/w).

The iodo-benzylether-PVA of the present invention may be either a iodo-benzylether-PVA wherein all the grafted iodinated benzyl groups are identical, or may be a iodo-benzylether-PVA, wherein the grafted iodinated benzyl groups are two or more different iodinated benzyl groups having different number of iodine atoms.

When the iodo-benzylether-PVA is grafted with identical iodinated benzyl groups, the iodine content (% I) of the iodo-benzylether-PVA of the present invention may be calculated from the degree of substitution (DS) as follows:

$$\% \ I = \frac{DS \times M_{(Iodine)} \times n}{\left[M_{(non\text{-}grafted)} \times (1 - DS)\right] + \left[M_{(grafted)} \times DS\right]} \times 100$$

wherein
$M_{(iodine)}$ represents the atomic mass of iodine atom (i.e. ~127)
n represents the number of iodine atoms per benzyl group (i.e. from 1 to 4)
$M_{(non\text{-}grafted)}$ represents the molar mass of a non-grafted repeating unit (i.e. ~44)
$M_{(grafted)}$ represents the molar mass of a grafted repeating unit (for example ~260 when the benzyl group has only one iodine as substituent, ~386 when the benzyl group has only two iodine atoms as substituents, ~512 when the benzyl group has only three iodine atoms as substituents, and ~638 when the benzyl group has only four iodine atoms as substituents).

When the iodo-benzylether-PVA of the present invention is grafted with two or more different iodinated benzyl groups having different number of iodine atoms, the iodine content (% I) of the iodo-benzylether-PVA of the present invention is the sum of the contributions of each type of grafted iodinated benzyl groups.

Therefore, the iodine content (% I) of a iodo-benzylether-PVA grafted with two or more different iodinated benzyl groups having different number of iodine atoms may be calculated by determining the degree of substitution (DS) for each type of iodinated benzyl groups, then by calculating the iodine content (% I) based on said DS using the above formula for each type of iodinated benzyl groups, and finally by adding the iodine contents (% I) calculated for each type of iodinated benzyl groups.

For instance, for a iodo-benzylether-PVA of the present invention having both mono-iodobenzyl groups and tri-iodobenzyl groups, the iodine content (% I) is the sum of the % I for the mono-iodobenzyl groups (n=1) plus the % I for the tri-iodobenzyl groups.

The iodine content may also be determined or confirmed by elemental analysis.

According to the present invention, the iodinated benzyl groups grafted on the poly(vinyl alcohol) must comprise 1-4 iodine atoms per benzyl group.

It is to be noted that in the present invention, the benzyl group may further comprise other substituents such as amino, amide, ester and/or carbamoyl groups in addition to iodine atom(s), but in a particularly preferred embodiment of the present invention, the benzyl group comprises only iodine atom(s) as substituent(s).

In one preferred embodiment of the present invention wherein all the grafted iodinated benzyl groups are identical, each benzyl group comprises only one iodine atom as substituent, and more preferably one iodine atom on the C4-position of the benzyl group.

In another preferred embodiment of the present invention wherein all the grafted iodinated benzyl groups are identical, each benzyl group comprises only three iodine atoms as substituents, and more preferably three iodine atoms on the C-2, C-3 and C-5 positions of the benzyl group.

However, each benzyl group may comprise from 1 to 4 iodine atoms, in any positions on the benzyl group.

In a preferred embodiment wherein the grafted iodinated benzyl groups are different iodinated benzyl groups having a different number of iodine atoms, the iodo-benzylether-PVA of the present invention have grafted thereon both iodinated benzyl groups comprising one iodine atom on the C4-position and iodinated benzyl groups comprising three iodine atoms on the C-2, C-3 and C-5 positions.

However, the iodo-benzylether-PVA of the present invention may have grafted thereon other types and combinations of iodinated benzyl groups, provided that said iodinated benzyl groups comprises 1-4 iodine atoms per benzyl group.

The average molar mass (M) of iodo-benzylether-PVA of the present invention is not particularly limited, and has to be determined depending on the chosen application.

Molar mass of the iodo-benzylether-PVA of the present invention may be easily controlled by appropriately selecting the molar mass (M) of the starting PVA polymer to be grafted in the process for preparing the iodo-benzylether-PVA of the present invention.

It is to be noted that a iodo-benzylether-PVA having a too high molar mass would not be appropriate for use as embolizing agent in an embolization composition because it would lead to an embolization composition too viscous for being injected via a catheter, and a iodo-benzylether-PVA having a too low molar mass would be not appropriate for use as embolizing agent in a liquid embolizing composition because the iodo-benzylether-PVA would not precipitate as a cohesive mass forming a solid or semi-solid embolic implant.

Further, it is to be noted that a iodo-benzylether-PVA having a high molar mass and therefore providing a high viscosity in solution is not preferable when used as embolizing agent in an embolizing composition because the embolizing composition should have a low concentration of embolizing agents in a high volume of solvent, which is not advantageous.

The average molar mass (M) of the iodo-benzylether-PVA of the present invention depends on the molar mass of the starting PVA polymer used to prepare the iodo-benzylether-PVA of the present invention and on the degree of substitution of the iodo-benzylether-PVA of the present invention.

The iodo-benzylether-PVA of the present invention may be prepared by an etherification reaction of PVA with a iodinated benzyl derivative.

More particularly, the iodo-benzylether-PVA of the present invention may be prepared by a process comprising reacting a 0-100% hydrolyzed poly(vinyl alcohol) (starting PVA) with a iodinated benzyl derivative comprising 1-4 iodine atoms per benzyl group in a polar aprotic solvent in the presence of a base in anhydrous conditions.

Poly(vinyl alcohol) (PVA) is a polymeric chain made of carbon atoms with pendant hydroxyl groups, which may also contain some pendant acetyl groups.

In the process of the present invention, a 0% hydrolyzed poly(vinyl alcohol) means a PVA containing 0% of pendant hydroxyl groups and 100% of pendant acetyl groups on the polymeric chain.

In the process of the present invention, a 100% hydrolyzed poly(vinyl alcohol) means a PVA containing only pendant hydroxyl groups.

It is to be noted that during the grafting reaction, pendant acetyl groups which may be present in the starting PVA are eliminated so that the iodo-benzylether-PVA of the present invention contains only pendant hydroxyl groups and pendant grafted iodinated benzyl ether groups.

In a particularly preferred embodiment of the present invention, the process for preparing the iodo-benzylether-PVA of the present invention comprises reacting a 75-100% hydrolyzed poly(vinyl alcohol) as the starting PVA with the iodinated benzyl derivative.

The average molar mass (M) of the starting PVA used in the process of the present invention is not particularly limited, and has to be determined depending on the average molar mass (M) expected for the final iodo-benzylether-PVA, depending on the chosen application.

However, performing the process of the present invention with a PVA having a too high molar mass or a too low molar mass would not lead to a iodo-benzylether-PVA appropriate for use as embolizing agent in a liquid embolizing composition.

Therefore, the average molar mass (M) of the starting PVA for preparing a iodo-benzylether-PVA for use as embolizing agent in a liquid embolizing composition is preferably not smaller than 5,000 Daltons and not greater than 200,000 Daltons, more preferably in the range from 10,000 to 130,000 Daltons, and still more preferably in the range from 10,000 to 50,000 Daltons.

For example, commercial PVA which may be used as starting PVA in the process of the present invention may be a PVA of pharmaceutical grade obtained from Sigma-Aldrich® Co. having a weight-average molar mass (Mw) of 13,000-23,000 Daltons and a degree of hydrolysis of 87-89%).

However, any commercial PVA having any degree of hydrolysis may be used for preparing the iodo-benzylether-PVA of the present invention according to the process of the present invention.

In the process of the present invention, the iodinated benzyl derivative is selected as a reagent to be grafted depending on the iodo-benzylether-PVA to be obtained, and may be for example a iodinated benzyl chloride, a iodinated benzyl bromide or a iodinated benzyl mesylate.

In a preferred embodiment, a iodo-benzylether-PVA comprising one iodine atom on the C4-position of all the benzyl groups may prepared by using commercial 4-iodobenzyl bromide (for example obtained from Sigma-Aldrich® Co.) as iodinated benzyl derivative.

In another preferred embodiment, a iodo-benzylether-PVA comprising three iodine atoms on the C-2, C-3 and C-5 positions on all the benzyl groups may be prepared by using 2,3,5-triiodobenzyl bromide as iodinated benzyl derivative.

2,3,5-Triiodobenzyl derivatives may be easily prepared as reported in the experimental part in Preparation Examples 1-4.

In another embodiment of the present invention, a iodo-benzylether PVA comprising both benzyl groups including one iodine atom on the C4-position and benzyl groups including three iodine atoms on the C-2, C-3 and C-5 positions may be prepared by using a mixture of 4-iodobenzyl bromide and 2,3,5-triiodobenzyl bromide as iodinated benzyl derivative.

However, a iodo-benzylether-PVA of the present invention having grafted thereon different benzyl groups may be prepared by using any mixture of two or more different iodinated benzyl derivatives comprising 1-4 iodine atoms per benzyl group.

The iodinated benzyl derivatives which may be used in the process of the present invention are either commercially available or may be easily prepared by the skilled person, for example from the corresponding iodinated benzoic acid or the corresponding iodinated benzyl alcohol according to conventional methods or according to methods based on those reported in the experimental part in Preparation Examples 1-4.

Examples of the polar aprotic solvent for use in the synthesis process of the present invention may include DMSO (dimethylsulfoxide), NMP (N-methylpyrrolidone) and THF (tetrahydrofuran).

Examples of the base for use in the process of the present invention may include NaOH, KOH and NaH, In a preferred embodiment of the process of the present invention, the polar aprotic solvent is NMP and the base is NaOH.

Kinetics studies have shown that the degree of substitution (DS) is dependent on the time of the grafting reaction and usually reaches a maximum value after approximately ½-15 hours so that the degree of substitution (DS) may be easily fixed by controlling the time of the grafting reaction.

If required, the iodo-benzylether-PVA of the present invention obtained by this process may be further purified by conventional techniques including, but not limited to, precipitation/solubilization/precipitation cycles to reach the degree of purity required.

The iodo-benzylether-PVA of the present invention is useful as embolizing agent in an injectable embolizing composition.

The injectable embolizing composition of the present invention comprises the iodo-benzylether-PVA of the present invention and a water-miscible, biocompatible solvent solubilizing the iodo-benzylether-PVA of the present invention.

Because the viscosity of a polymer solution is known to be very sensitive to polymer molar mass, particularly at high concentration, it is important to appropriately select the molar mass of the iodo-benzylether-PVA contained in the embolizing composition in order that it is not too high and not too low for this application.

For example, with respect to its molar mass, a preferable iodo-benzylether-PVA for use as embolic agent in an embolizing composition may be obtained by using, as starting PVA, a PVA having a molar mass not smaller than 5,000 Daltons and not greater than 200,000 Daltons, preferably in the range from 10,000 to 130,000 Daltons, and more preferably in the range from 10,000 to 50,000 Daltons.

The concentration of a polymer in solution also affects not only the viscosity of the polymer solution but also the precipitation behaviour of the polymer.

The concentration of the iodo-benzylether-PVA of the present invention in the embolizing composition is selected in the range of 5-65 w/w %, said selection being dependent on the targeted viscosity of the embolizing composition, which itself depends on the average molar mass of the iodo-benzylether-PVA of the present invention used in the embolizing composition.

According to the present invention, said selection of the concentration of the iodo-benzylether-PVA of the present invention must lead to an embolizing composition which is injectable, i.e. which is not too viscous for being injected, and further which is capable of forming a cohesive solid or semi-solid mass upon contact with an aqueous media such as a body fluid by precipitation of the iodo-benzylether-PVA.

Preferably, the concentration of the iodo-benzylether-PVA of the present invention is selected to be as high as possible in order to provide an embolizing composition having a reduced quantity of solvent.

In a particularly preferred embodiment of the present invention, the concentration of the iodo-benzylether-PVA of the present invention in the embolizing composition is selected in the range of 20-50 w/w %.

Further, it is preferable that the iodo-benzylether-PVA of the present invention used in the injectable embolizing composition of the present invention has a iodine content (% I) of at least 20% (w/w), and more preferably of at least 40% (w/w) in order to provide an improved radiopacity to the embolizing composition and also to the embolic mass formed by precipitation of the iodinated-benzylether-PVA upon contact of the embolizing composition with a body fluid.

The water-miscible, biocompatible solvent used in the injectable embolizing composition of the present invention is not particularly limited, provided that it solubilizes the iodo-benzylether-PVA to form a homogeneous solution.

In a preferred embodiment, the water-miscible, biocompatible solvent is selected from dimethylsulfoxide, N-methylpyrrolidone, glycofurol, pyrrolidone, ethanol, propylene glycol, polyethylene glycol, Solketal™, glycerol formal, tetrahydrofurfuryl alcohol, dimethyl isosorbide, ethyl lactate, hydroxyethyllactamide and N,N-dimethylacetamide, and more preferably from dimethylsulfoxide (DMSO), N-methylpyrrolidone (NMP) and glycofurol.

According to an embodiment of the present invention, the injectable embolizing composition of the present invention comprises one iodo-benzylether-PVA of the present invention.

In a preferred embodiment, the iodo-benzylether-PVA of the present invention contained in the injectable embolizing composition of the present invention is a iodo-benzylether-PVA, wherein each benzyl group comprises one iodine atom on C-4 position (called "4-mono-iodobenzylether-PVA" or "MIB-PVA" below).

In another preferred embodiment, the iodo-benzylether-PVA of the present invention contained in the injectable embolizing composition of the present invention is a iodo-benzylether-PVA wherein each benzyl group comprises 3 iodine atoms on C-2, C-3 and C-5 positions (called "2,3,5-tri-iodo-benzylether-PVA" or "TIB-PVA" below).

According to another embodiment of the present invention, the injectable composition of the present invention may comprise two or more different iodo-benzylether-PVAs of the present invention having different number or different position of iodine atoms, provided that the total concentration of the iodo-benzylether-PVAs of the present invention contained in the injectable embolizing composition is selected in the range of 5-65 w/w %.

In a preferred embodiment, the injectable embolizing composition of the present invention contains 4-mono-iodobenzylether PVA (MIB-PVA) and 2,3,5-tri-iodobenzylether-PVA (TIB-PVA) in variable proportions.

The viscosity and mechanical properties of iodo-benzylether-PVA, based on, for instance, 4-monoiodo-benzylether-PVA (MIB-PVA) or 2,3,5-triiodo-benzylether-PVA (TIB-PVA) are quite different.

4-Monoiodo-benzylether-PVA (MIB-PVA) is a softer material than 2,3,5-triiodo-benzylether-PVA (TIB-PVA), it is less fragile and brittle due to its lower glass transition temperature (Tg of MIB-PVA: 55° C., TIB-PVA: 111° C.).

In addition, solutions of 2,3,5-triiodo-benzylether-PVA (TIB-PVA) in NMP tend to precipitate faster in aqueous environment than 4-monoiodo-benzylether PVA (MIB-PVA).

Therefore, mixtures of MIB-PVA and TIB-PVA in variable proportions can be used to adjust the mechanical properties of the final precipitated implant.

For instance, equal proportions of MIB-PVA and TIB-PVA dissolved in NMP show formulation viscosity, precipitation time and mechanical properties intermediate between that of MIB-PVA and TIB-PVA.

Blend of MIB-PVA: TIB-PVA can therefore generate a family of liquid embolizing compositions, as illustrated in the Example 14.

Tailoring implant properties can also be obtained using PVA polymers based on two or more kind of iodinated repeating units.

For instance, as illustrated in Example 13, PVA polymer grafted with MIB and TIB can be obtained by mixing in the reaction vial equal molar quantities of mono-iodobenzyl derivative and tri-iodobenzyl derivative. The resulting copolymer MTIB-PVA shows a close to 50:50 molar ratio of 4-mono-iodobenzylether and 2,3,5-tri-iodobenzylether grafted groups, corresponding to a 38:62 MIB:TIB mass ratio.

Such a copolymer MTIB-PVA has a glass transition temperature (Tg=68° C.) intermediate between that of MIB-PVA and TIB-PVA, and Example 15 shows that precipitation also results in intermediate properties between that of MIB-PVA and TIB-PVA.

Likewise, based on copolymers, a whole family of formulations can be obtained, tailoring liquid embolic properties by adapting copolymer molar mass, concentration and MIB/TIB ratio.

A man skilled in the art will be capable to determine easily if the composition containing the selected concentration of the iodo-benzylether-PVA of the present invention and the selected water-miscible, biocompatible solvent is appropriate for use as an embolizing composition by carrying out a precipitation test of the composition in water.

The injectable embolizing composition of the present invention is particularly useful when used for forming in-situ a cohesive solid or semi-solid mass in a blood vessel or into a tumor for treating human or other mammalian subjects.

When the embolizing composition of the present invention is used for embolizing blood vessels, in particular for treating lesions such as aneurysms, arteriovenous malformations, arteriovenous fistula, and tumors, it is introduced into the blood vessel via a catheter delivery means under fluoroscopy so that after precipitation of the iodo-benzylether-PVA, the blood vessel is embolized by the embolic mass formed by the precipitated iodo-benzylether-PVA.

When the embolizing composition of the present invention is used in the treatment of tumors by direct puncture, it is directly injected into the tumoral tissue via a needle technology so that after precipitation of the iodo-benzylether-PVA, tumor is filled with the embolic mass formed by the precipitated iodo-benzylether-PVA.

The particular amount of the embolizing composition employed is dictated by the total volume of the vasculature or tissue to be embolized, the concentration of the iodo-benzylether-PVA, the rate of precipitation of the iodo-benzylether-PVA, etc.; the determination of such factors lies well within the competence of a person skilled in the art.

In an embodiment of the present invention, the injectable embolizing composition of the present invention comprises drugs or biopharmaceuticals.

The injectable embolizing composition including drugs or biopharmaceuticals is particularly useful for forming in-situ a cohesive solid or semi-solid mass loaded with said drugs or biopharmaceuticals and able to subsequently deliver in-situ by release the drugs or biopharmaceuticals.

Example 17 illustrates the release of an anticancer agent, doxorubicine hydrochloride, from the precipitated cohesive mass obtained when an injectable embolizing composition of the present invention including the anticancer agent is used.

In another embodiment of the present invention, the injectable embolizing composition comprises superparamagnetic iron oxide nanoparticles (SPIONs).

The injectable embolizing composition including SPIONs is particularly useful for forming in-situ a solid or semi-solid implant loaded with said SPIONs into a tumor for treating the tumor by hyperthermia.

SPIONs which are used in the injectable embolizing composition of the present invention may be adequately coated or encapsulated, or may be immobilized in silica beads.

SPIONs which may be included in the injectable embolization composition of the present invention may be commercially available SPIONs, for example SPIONs immobilized in silica beads such as MagSilica 50-85 (Evonik, Germany), or may be for example SPIONS as disclosed in WO-A-2006/125452 or by Matthieu Chastellain et al. "*Superparamagnetic Silica-Iron Oxide Nanocomposites for Application in Hyperthermia*" in Advanced Engineering Materials, 6:235-241, 2004.

Figure 12:
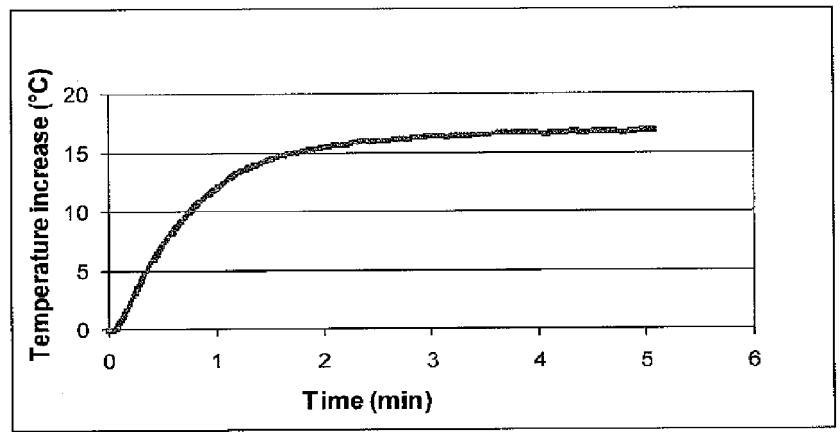
FIG. 12 represents a graph illustrating the temperature increase obtained with the hyperthermic implant shown in FIG. 11b under exposure to an alternating magnetic field.

Example 16 illustrates the in-situ formation of an hyperthermic implant by using the injectable embolizing composition of the present invention loaded with SPIONs immobilized in silica bead for controlled local hyperthermia, FIG. 12 represents a graph showing that when the hyperthermic implant obtained in Example 16 is exposed to an alternating magnetic field, the temperature increases, thus demonstrating that the injectable embolizing composition of the present invention loaded with SPIONs is applicable for treatment, for example of a tumor, by hyperthermia.

In another embodiment of the present invention, the injectable embolizing composition of the present invention may be used for forming in-situ a semi-solid implant for treating urinary incontinence through local tissue augmentation.

For instance, in the context of the treatment of urinary incontinence, a widespread condition among women, urethral bulking is recognized as a standard treatment.

It consists in injecting, under the bladder mucosa, a biomaterial that creates a bulge in the tissue, thus increasing the closure of the urethra. Collagen is used nowadays but its effect last only for a few months.

Consequently, there is a need for long-lasting, non-degradable implants which should offer imaging ability for long-term follow-up.

Therefore, the injectable embolizing composition of the present invention provides an efficient alternative.

The present invention also concerns a coating composition for forming a coating on medical device comprising the iodo-benzylether-PVA of the present invention and a solvent solubilizing the iodo-benzylether-PVA, wherein the concentration of the iodo-benzylether-PVA in the composition is selected in the range from 5-85% so that the composition is capable of forming a radiopaque coating after application on a medical device and solvent evaporation.

The coating composition of the present invention can be used to deposit a radiopaque coating onto medical devices to make them visible under x-ray imaging.

Fabrication of the coating can be obtained by deposition of the coating composition of the present invention followed by drying.

The thickness of the coating will depend on several factors, among them the viscosity of the coating composition.

In the coating composition of the present invention, the solvents which may be used for solubilizing the iodo-benzylether-PVA comprise tetrahydrofuran, dimethylformamide, dichloromethane, N-methylpyrrolidone, dimethyl sulfoxide.

In the case of poorly biocompatible solvent such as dichloromethane, complete elimination of the solvent must be obtained before use, which can be obtained by drying for organic solvents having a low boiling point.

Figure 14:
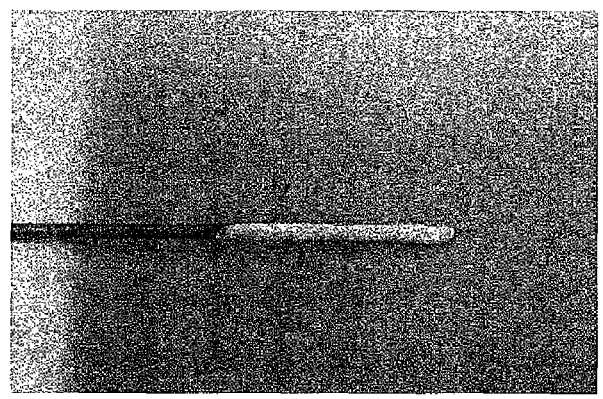
FIG. 14 represents a catheter coated with a coating composition of the present invention as reported in Example 18.

For example, said coating composition may be useful for coating the tip of a catheter, as reported in Example 17 and illustrated in FIG. 14.

The present invention further concerns particles, such as nanoparticles and microparticles made of the iodo-benzylether-PVA of the present invention.

Nanoparticle or microparticles can be produced to help or improve the use of x-ray imaging techniques in the medical field.

For example, radiopaque particles of the present invention may be used as contrast agent to tag a specific tissue or to follow, upon injection, the flow of a physiological fluid.

In a preferred embodiment, the radiopaque particles of the present invention further contain drugs or pharmaceuticals.

Radiopaque particles loaded with drugs or biopharmaceuticals can be tracked into the body after their administration, for example after intratumoral injection.

Radiopaque particles of the present invention can be produced from the iodo-benzylether-PVA of the present invention using any technique known to those skilled in the art of particle manufacturing.

For instance, Example 19 provides means for the fabrication of nanoparticles of different sizes from MIB-PVA 47 kDa (DS=49%) and TIB-PVA 13 kDa (DS=53%) using the nanoprecipitation technique.

The following examples are intended to illustrate the present invention. However, they cannot be considered in any case as limiting the scope of the present invention.

EXAMPLES

The reactions can be monitored by thin layer chromatography (TLC) on silica with ⅓ ethyl acetate/hexane mixture as mobile phase and observation under UV, illumination at 254 nm wavelength.

$^1$H and $^{13}$C NMR spectra were recorded on a Brucker 300 MHz and Brucker 400 MHz spectrometer respectively. Chemical shifts are given in ppm (reference $\delta$=7.27 (CDCl$_3$), 2.50 (DMSO-d6) for $^1$H-NMR and $\delta$=77.1 (CDCl$_3$), 39.5 (DMSO-d6) for $^{13}$C-NMR).

The degree of substitutions (DS) were calculated from the integration of the NMR lines of the $^1$H-NMR spectra of the iodo-benzylether-PVA.

The iodine contents were calculated based on the degree of substitution, as explained in the description and confirmed by elemental analysis.

Radiopacities of iodo-benzylether-PVA were evaluated under X-ray visualization of powdered samples and solutions.

Transmission IR spectra were recorded on a Nicolet 460 Spectrometer ESP. Pellets were prepared by pressing 1 mg of compound and 100 mg KBr powders.

Melting points were determined by differential scanning calorimetry (DSC) on a 0200, TA Instrument.

PVA 13 kDa is a poly(vinyl alcohol) having a weight-average molar mass (Mw) of 13,000-23,000 Daltons and a degree of hydrolysis of 87-89% et was purchased from Sigma-Aldrich® Co.

PVA 47 kDa is Mowiol® 6-98, a poly(vinyl alcohol) having a weight-average molar mass (Mw) of 47,000 Daltons, a degree of hydrolysis of 98.0-98.8%, and a viscosity of 6 mPa·s at 4% in $H_2O$, 20° C. and was purchased from Sigma-Aldrich® Co.

PVA 61 kDa is Mowiol® 10-98, a poly(vinyl alcohol) having a weight-average molar mass (Mw) of 61'000 Daltons, a degree of hydrolysis of 98.0-98.8%, and a viscosity of 10 mPa·s at 4% in $H_2O$, 20° C. and was purchased from Sigma-Aldrich® Co.

PVA 125 kDa is Mowiol® 20-98, a poly(vinyl alcohol) having a weight-average molar mass (M) of 12'500 Daltons, a degree of hydrolysis of 98.0-98.8%, and a viscosity of 20 mPa·s at 4% in $H_2O$, 20° C. and was purchased from Sigma-Aldrich® Co.

2,3,5-triiodobenzoic acid was purchased from Changzhou Dahua Imp. And Exp. Corp. Ltd. (China).

4-iodobenzyl bromide was purchased from Sigma-Aldrich® Co.

Other reagents were purchased from commercial suppliers and used as received unless otherwise is noted.

THF and $CH_2Cl_2$ were dried by passing them on a basic activated alumina, $Al_2O_3$.

$H_2O$ means de-ionized water.

Preparation Example 1

Synthesis of 2,3,5-triiodobenzyl alcohol

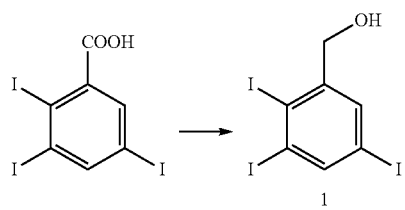 [SMILES: O=C(O)c1cc(I)cc(I)c1I ; OCc1cc(I)cc(I)c1I]

A solution (1M) of $BH_3$-tetrahydrofuran (75 ml, 75 mmol) was added dropwise to a solution of 2,3,5-triiodobenzoïc acid (5 g, 10 mmol) in dry tetrahydrofuran (10 ml) keeping the temperature inside the reactor below 2° C. under dry nitrogen gas flow. The reaction mixture was stirred 1 h15 at 0° C., then 1 h at room temperature (18° C.), and a white precipitate was obtained. Then a cold solution tetrahydrofuran/$H_2O$ 13:2 (26 ml) was slowly added to the crude mixture (temperature monitored in cooling the reactor) for hydrolysis of excess boran and the crude mixture was neutralized by dilution in a cold solution of $NaHCO_3$ (~100 ml). A white precipitate appeared after a stirring of 1 h. The solid was recovered by filtration and washed with $H_2O$ and cold absolute ethanol. In order to eliminate traces of ethanol after evaporation, the white solid was dissolved in $CH_2Cl_2$ then evaporated then dried under vacuum. 2,3,5-triiodobenzyl alcohol in the form of a white clean solid was obtained in quantitative yield (4.8 g).

Mp: 156-159° C.

IR: 3186, 2904, 1524, 1400, 1368, 1235, 1144, 1047, 997, 859, 719, 675 cm$^{-1}$ $^1$H-NMR (DMSO-d6): 8.16 (d, 1H, J=2.0 Hz), 7.70 (d, 1H, J=2.0 Hz), 5.69 (Is, 1H, OH), 4.34 (s, 2H, $CH_2$)

$^{13}$C-NMR (DMSO-d6): 69.83 ($CH_2$), 95.77 (Cq), 109.84 (Cq), 112.99 (Cq), 134.56 (CH), 144.13 (Cq), 149.27 (CH)

Preparation Example 2

Synthesis of 2,3,5-triiodobenzyl mesylate 2

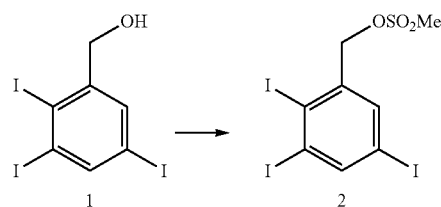

Mesyl chloride (0.6 ml, 8 mmol) was added dropwise to a suspension of 2,3,5-triiodobenzyl alcohol 1 (1.94 g, 4 mmol) in dry dichloromethane (30 ml) containing diisopropylethylamine (1.4 ml, 8 mmol) at 0° C. under dry nitrogen gas flow. The reaction mixture was stirred 1 h15 at 0° C., then cold $H_2O$ (40 ml) was added. The resulting aqueous phase was extracted with dichloromethane (10 ml). The combined organic extracts were washed with $H_2O$ (8 ml) then dried ($Na_2SO_4$), filtered and concentrated. The pale yellow solid was also washed with cold methanol (35 ml). 1.894 g of 2,3,5-triiodobenzyl mesylate in the form of a white clean solid was obtained in 84% yield.

Mp: 130-133° C.

IR: 3026, 1525, 1342, 1330, 1176, 1168, 1008, 975, 862, 836 cm$^{-1}$ $^1$H-NMR (CDCl$_3$): 8.23 (d, 1H, J=1.5 Hz), 7.69 (d, 1H, J=1.5 Hz), 5.23 (s, 2H, $CH_2$), 3.11 (s, 31-1, Me)

$^{13}$C-NMR (CDCl$_3$): 38.29 (Me), 76.32 ($CH_2$), 94.72 (Cq), 110.98 (Cq), 112.29 (Cq), 136.96 (CH), 140.69 (Cq), 147.48 (CH)

Preparation Example 3

Synthesis of 2,3,5-triiodobenzyl bromide 3

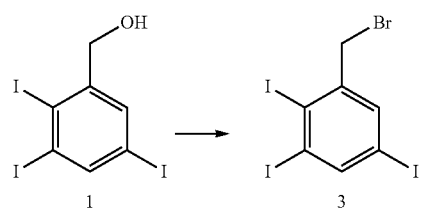 [SMILES: OCc1cc(I)cc(I)c1I ; BrCc1cc(I)cc(I)c1I]

A solution of phosphorous tribromide (3.8 ml, 40 mmol) was added dropwise to a solution of 2,3,5-triiodobenzyl alcohol 1 (9.72 g, 20 mmol) in dry tetrahydrofuran (50 ml) at 0° C. under dry nitrogen gas flow. The reaction mixture was stirred 5 minutes at 0° C., then 20 minutes at room temperature (18° C.), then cold H₂O/DCM (60160 ml) was added. The resulting aqueous phase was extracted with dichloromethane (2×10 ml). The combined organic extracts were washed with NaHCO₃ aq (20 ml) and H₂O (20 ml) then dried (Na₂SO₄), filtered and concentrated. The white solid was also washed with cold methanol (45 ml). 9.35 g of 2,3,5-triiodobenzyl bromide in the form of a white clean solid was obtained in 85% yield.

Mp: 120-121° C.

IR: 710, 866, 980, 1157, 1212, 1398, 1515, 3026 cm$^{-1}$ $^1$H-NMR (DMSO-d6): 4.81 (s, 2H, CH₂), 7.95 (d, 1H, J=2.1 Hz), 8.18 (d, 1H, J=2.1 Hz)

$^{13}$C-NMR (DMSO-d6): 42.33 (CH₂), 95.77 (Cq), 113.95 (Cq), 114.97 (Cq), 137.69 (CH), 144.87 (Cq), 145.92 (CH)

Preparation Example 4

Synthesis of 2,3,5-triiodobenzyl chloride 4

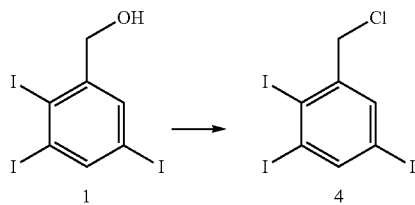 [SMILES: OCc1cc(I)cc(I)c1I ; ClCc1cc(I)cc(I)c1I]

Mesyl chloride (4.24 ml, 56 mmol) was added dropwise into a suspension of 2,3,5-triiodobenzyl alcohol 1 (9.72 g, 20 mmol) in dry dichloromethane (140 ml) containing diisopropylethylamine (11 ml, 64 mmol) and lithium chloride (4.24 g, 100 mmol) at 0° C. under dry nitrogen gas flow. The reaction mixture was stirred 5 h at room temperature, then cold H₂O (100 mL) was added. The resulting aqueous phase was extracted with dichloromethane (2×10 ml). The combined organic extracts were washed with NaHCO₃ aq (20 ml) and H₂O (20 ml) then dried (Na₂SO₄), filtered and concentrated. The pale yellow solid was also washed with cold absolute ethanol (25 mL). 9.05 g of 2,3,5-triiodobenzyl chloride in the form of a white clean solid was obtained in 90% yield.

Mp: 97-98° C.

IR: 680, 731, 859, 867, 1007, 1133, 1267, 1371, 1439, 1520 cm$^{-1}$ $^1$H-NMR (DMSO-d6): 4.87 (s, 2H, CH₂), 7.92 (d, 1H, J=1.9 Hz), 8.21 (d, 1H, J=1.9 Hz)

$^{13}$C-NMR (DMSO-d6): 53.58 (CH₂), 95.78 (Cq), 113.89 (Cq), 114.65 (Cq), 137.74 (CH), 144.48 (Cq), 146.08 (CH)

Preparation Example 5

Synthesis of 2,3,5-tri-iodobenzoate-PVA 13 kDa (TIB/Ester-PVA 13 kDa)

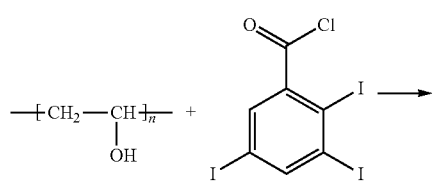

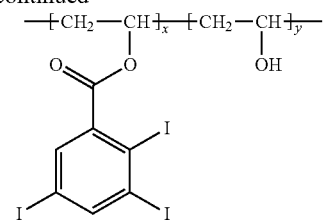

The grafting reaction was adapted from the work reported in "Elaboration of radiopaque iodinated nanoparticles for in situ control of local drug delivery" D. Mawad, H. Mouaziz, A. Penciu, H. Méhier, B. Fenet, H. Fessi, Y. Chevalier; *Biomaterials* 2009, 30, 5667-5674.

The PVA 13 kDa was dissolved in dry NMP under nitrogen gas flow and a solution of triiodobenzoyl chloride in NMP was added. Then dry pyridine and DMAP were added. After 12 hours, cold water was added, a paste material precipitated, was filtered and washed with methanol. For the purification step, the crude paste material was dissolved in NMP (concentration: 22 wt %) and cold ethanol was added. A paste material precipitated, was filtered and analyzed by NMR spectrum. The 1H NMR spectrum showed the grafted PVA free of residual reagent, and traces of solvents. In order to eliminate the traces of solvents, the grafted PVA was dissolved in THF (concentration: 30 wt %) and cold water was added. A paste material precipitated, was filtered, washed with methanol and dried under vacuum. The grafted PVA was obtained as a brown solid.

$^1$H-NMR (DMSO-d6): 1.35-1.95 ppm (m, 5.81 au, CH₂ PVA chain, 2(x+y)), 3.81 ppm (s, 2.09 au, CH$_b$ PVA chain, y), 4.21-4.67 ppm (m, 2.69 au, OH), 5.37 (s, 0.78 au, CH$_a$ PVA chain, x), 7.71 ppm (s, 1.0 au, H aromatic, x), 8.34 ppm (s, 1.0 au, H aromatic, x)

Based on NMR spectrum, TIB/Ester-PVA 13 kDa was obtained with a DS of 34%.

Preparation Example 6

Synthesis of 4-mono-iodobenzoate-PVA 47 kDa (MIB/Ester-PVA 47 kDa)

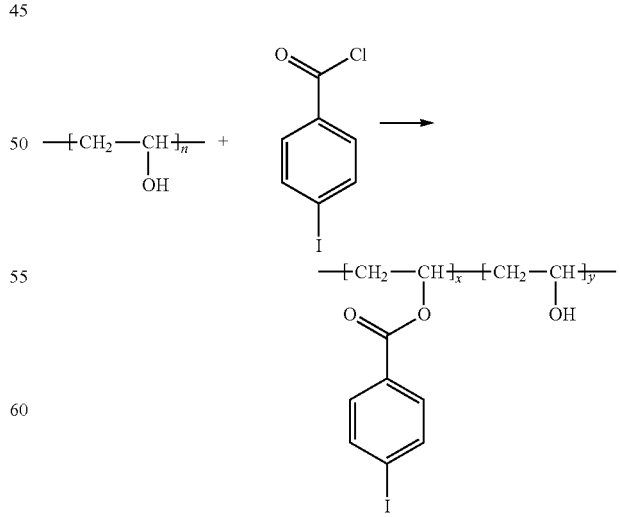

The reaction conditions were the same as used for the 2,3,5-tri-iodobenzoate-PVA 13 kDa in Preparation Example 5. The PVA was dissolved in NMP and a solution of 4-mono-iodobenzoyl chloride was added. Then dry pyridine and DMAP were added. After 6 hours, cold water was added and a paste material has precipitated, was filtered and washed with methanol. For the purification step, the crude paste material was dissolved in NMP (concentration: 14 wt %) (the mixture is yellow but opaque and all of the particles are dissolved) and 100 mL of a solution of $NaHCO_3$ was added. A solid has precipitated, was filtered and washed with methanol. This step was repeated until the monoiodobenzoyl chloride was eliminated. Then the solid was dissolved in NMP (concentration: 19 wt %) and cold water was added. A solid has precipitated, was filtered and washed with methanol. The solid was analyzed by $^1$H-NMR.

$^1$H NMR (DMSO-d6): 1.05-2.4 ppm (m, 5.49 au, $CH_2$ PVA chain, 2(x+y)), 3.81 ppm (s, 1.28 au, $CH_b$ PVA chain, y), 4.21-4.67 ppm (m, 0.77 au, 01-1), 5.37 ppm (s, 1.0 au, $CH_a$ PVA chain, x), 7.10-7.90 ppm (m, 4.35 au, H aromatic, 4x)

Based on NMR spectrum, MIB/Ester-PVA 47 kDa was obtained with a DS of 40%.

Example 1

Grafting 2,3,5-triiodobenzyl bromide to PVA to prepare 2,3,4-triiodobenzyl ether of poly(vinyl alcohol) of the present invention (TIB-PVA 13 kDA)

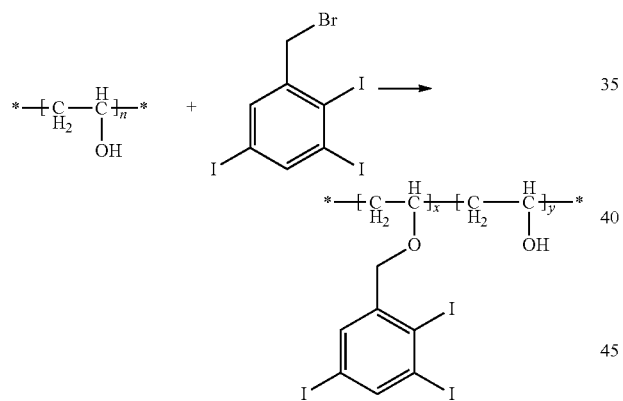

294 mg of PVA 13 kDa (6 mmol) was dissolved in 20 ml of dry NMP (concentration of PVA: 0.3 M) under nitrogen gas flow. The reaction mixture was stirred for 5 minutes at 130° C.; then the temperature was decreased to 50° C. 4.94 g of 2,3,5-triiodobenzylbromide 3 (9 mmol) was added and the reaction mixture was stirred for 10 minutes. Then, 480 mg of ground and dried NaOH (12 mmol) was added in 10 minutes. After 5 hours, the mixture was cooled to room temperature and 20 ml of cold water was added under stirring. A solid precipitate has appeared and was filtrated, washed with methanol and dichloromethane. 3.15 g of crude solid was obtained and analyzed by $^1$H-NMR to determine that the crude product contained 56% of non-grafted triiodo-benzylbromide and 30% of grafted PVA. In order to isolate the grafted PVA, the crude solid was dissolved in NMP (concentration: 7 wt %) and same volume of cold methanol was added. A paste material precipitated and was filtrated, washed with methanol and was analyzed by $^1$H NMR. The purity of grafted PVA was 86%. This paste material was dissolved in NMP (concentration: 17 wt %) and same volume of cold methanol was added. A paste material precipitated, was filtrated, washed with methanol and was analyzed by $^1$H NMR. The purity of grafted PVA was 97%. In order to obtain a purity of 100%, the paste material was dissolved in NMP (concentration: 17 wt %) and same volume of cold water was added. The solid precipitate was filtrated, washed with methanol to obtain the grafted PVA in the form of a beige solid with a purity of 100%, as analyzed by NMR with a overall yield of 19%.

In order to eliminate residual traces of NMP contained in the grafted PVA, the grafted PVA was dissolved in THF (concentration: 13 wt %) and cold water was added. The grafted PVA (TIB-PVA 13 kDa) has precipitated and was analyzed by $^1$H-NMR.

The $^1$H-NMR spectrum is represented in FIG. 1 and shows traces of THF in the grafted PVA.

$^1$H-NMR (DMSO-d6): 1.51-1.85 (m, 3.8 au, $CH_2$ PVA chain (2(x+y)), 3.4-4.05 (m, 1.5 au, CH PVA chain (x+y)), 4.16-4.52 (m, 2.4 au, $CH_2$ benzyl and residual OH (2x+y)), 7.60 (s, 1.0 au, H aromatic (x)), 8.04 (s, 1.0 au, H aromatic (x))

The degree of substitution (DS) was measured from the areas under the peaks of the NMR spectrum calculated from the integration of the NMR lines. The ratio of the area of the aromatic lines to the area of the $CH_2$ of PVA chain is x/2(x+y)=DS/2. Accordingly, DS was 0.54 (i.e DS=54%).

The expected iodine content as calculated from the DS was 69%, and the iodine content as confirmed by elemental analysis was 64%.

Example 2

Grafting 4-monoiodobenzyl bromide to PVA to prepare 4-monoiodobenzyl ether of poly(vinyl alcohol) of the present invention (MIB-PVA 13 kDa)

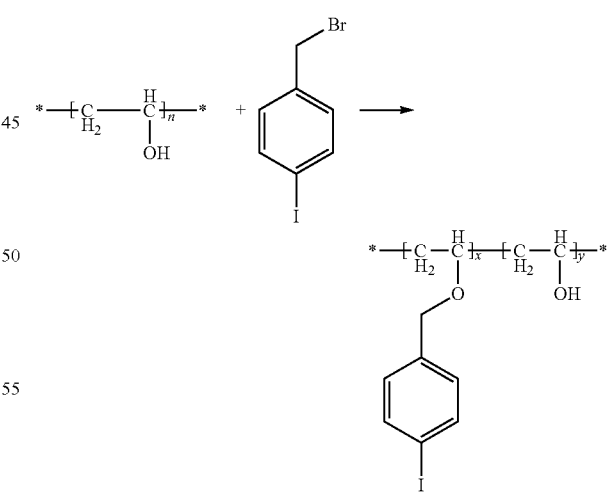

Figure 2:
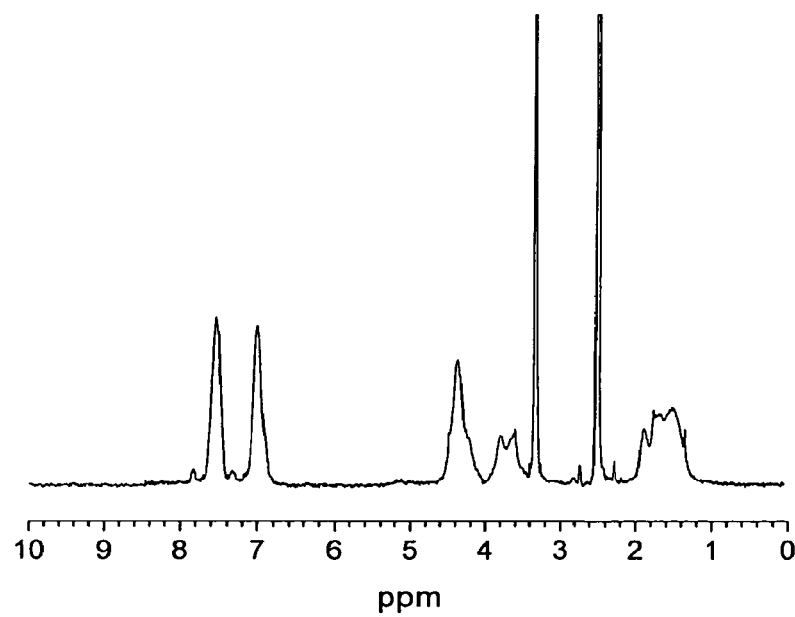
FIG. 2 shows the $^1$H-NMR spectrum of 4-iodobenzylether of poly(vinyl alcohol) of the present invention prepared according to Example 2.

589 mg of PVA 13 kDa (12 mmol) was dissolved in 40 ml of dry NMP under nitrogen gas flow. The reaction mixture was stirred for 5 minutes at 130° C.; then the temperature was decreased to 50° C. 5.3 g of 4-iodobenzyl bromide (18 mmol) was added and the reaction mixture was stirred for 10 minutes. Then, 960 mg of ground and dried NaOH (24 mmol) was added in 10 minutes. After 4 hours, the mixture was cooled to room temperature and 40 ml of cold water was added under stirring. A paste material has appeared and was filtrated, washed with methanol and dichloromethane. 3.9 g of crude paste material was obtained and analyzed by $^1$H NMR to determine that the paste material contained 44% of non-grafted 4-iodobenzyl bromide and 56% of grafted PVA. In order to isolate the grafted PVA, the paste material was dissolved in DMF (concentration: 50 wt %) and two volumes of cold methanol was added. A paste material has precipitated and was filtrated, washed with methanol and was analyzed by $^1$H-NMR. The purity of grafted PVA was 80%. This paste material was dissolved in THF (concentration: 50 wt %) and three volumes of cold methanol was added. A paste material has precipitated, was filtrated, washed with methanol and was analyzed by $^1$H NMR. The purity of grafted PVA was 95%. The paste material was dissolved in THF (concentration: 28 wt %) and two volumes of cold methanol was added. A paste material has appeared, was filtrated, and washed with methanol. The purity was 98%. In order to obtain a purity of 100%, the grafted PVA was dissolved in THF (concentration: 29 wt %) and three volumes of cold water was added. A paste material has appeared, was filtrated, and washed with methanol. After drying, the grafted PVA (MIB-PVA 13 kDa) was obtained in the form a an orange solid in an overall yield of 24%. The $^1$H NMR spectrum of the MIB-PVA 13 kDa is represented in FIG. 2.

$^1$H-NMR (DMSO-d6): 1.34-1.90 (m, 3.8 au, $CH_2$ PVA chain (2(x+y)), 3.58-3.78 (m, 1.5 au, CH PVA chain (x+y)), 4.23-4.48 (m, 2.4 au, $CH_2$ benzyl and residual OH (2x+y)), 7.00 (s, 2.0 au, H aromatic (2x)), 7.54 (s, 2.0, H aromatic (2x))

The degree of substitution (DS) was measured from the areas under the peaks of the NMR spectrum calculated from the integration of the NMR lines. The ratio of the area of the aromatic lines to the area of the $CH_2$ of PVA chain is 2x/2(x+y)=DS. Accordingly, DS was 0.56 (i.e DS=56%).

The expected iodine content as calculated from the IDS was 43%, and the iodine content confirmed by elemental analysis was 43%.

Example 3

Precipitation Tests

The TIB-PVA 13 kDa obtained in Example 1 was dissolved in NMP at concentrations of 10% w/w and 33% w/w, and these two injectable compositions were precipitated in water using a syringe with a needle of 0.8 mm diameter. The results obtained are shown in FIG. 3a and FIG. 3b.

Figure 3A:
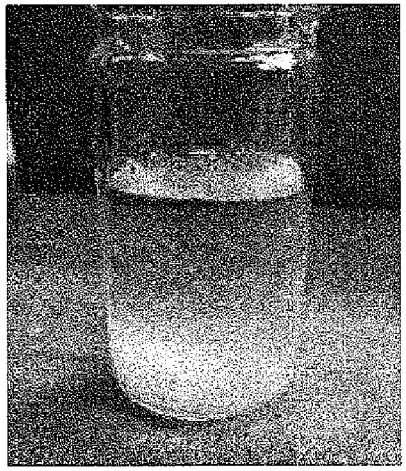
FIG. 3a is a photograph showing precipitation in water of 2,3,5-triiodobenzylether of poly(vinyl alcohol) prepared according to Example 1 dissolved at a concentration of 10% w/w in N-methylpyrrolidone (NMP).

As shown in FIG. 3a, the injectable composition containing 10% w/w of TIB-PVA 13 kDa dissolved in NMP did not precipitate as a cohesive mass, and therefore is not appropriate as injectable embolizing composition of the present invention.

Figure 3B:
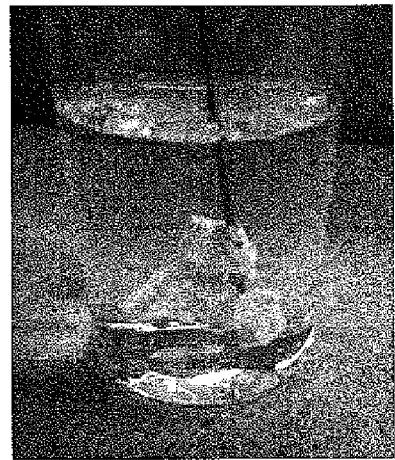
FIG. 3b is a photograph showing precipitation in water of 2,3,5-triiodobenzylether of poly(vinyl alcohol) prepared from PVA 13 kDa according to Example 1, dissolved at a concentration of 33% w/w in NMP.

However, as shown in FIG. 3b, the injectable composition containing 33% of TIB-PVA 13 kDa dissolved in NMP precipitates as a cohesive mass, and therefore is appropriate as injectable embolizing composition of the present invention.

Further, the MIB-PVA 13 kDa obtained in Example 2 was dissolved in DMSO at a concentration of 33% w/w and this injectable composition was precipitated in water using a syringe of 1 ml with a needle of 0.9 mm.

Figure 4:
FIG. 4 is a photograph showing precipitation in water of 4-iodobenzylether of poly(vinyl alcohol) prepared from PVA 13 kDa according to Example 2, dissolved at a concentration of 33% w/w in DMSO.

As shown in FIG. 4, the injectable composition containing 33% w/w of MIB-PVA dissolved in DMSO precipitates as a cohesive mass, and therefore is appropriate as injectable embolizing composition of the present invention.

Additional experiments shown that all compositions containing TIB-PVA 13 kDa dissolved in NMP or MIB-PVA 13 kDa dissolved in DMSO precipitate as a cohesive mass for concentrations higher than 20% (w/w).

Example 4

Embolizing Compositions and Viscosities

As the viscosity is an important parameter for the choice of the concentration of the iodo-benzylether-PVA in injectable compositions for embolization, the following experiments have been performed.

The MIB-PVA 13 kDa obtained in Example 2 was dissolved in DMSO at concentrations varying from 20 to 50% w/w, and the viscosities of the solutions were measured.

The TIB-PVA 13 kDa obtained in Example 1 was dissolved in NMP at concentrations varying from 20 to 50% w/w, and the viscosities of the solutions were measured.

Viscosities were measured at a temperature of 25° C. using a cone-plate rheometer (Bohlin CV0120 from Malvern Instruments).

Figure 5:
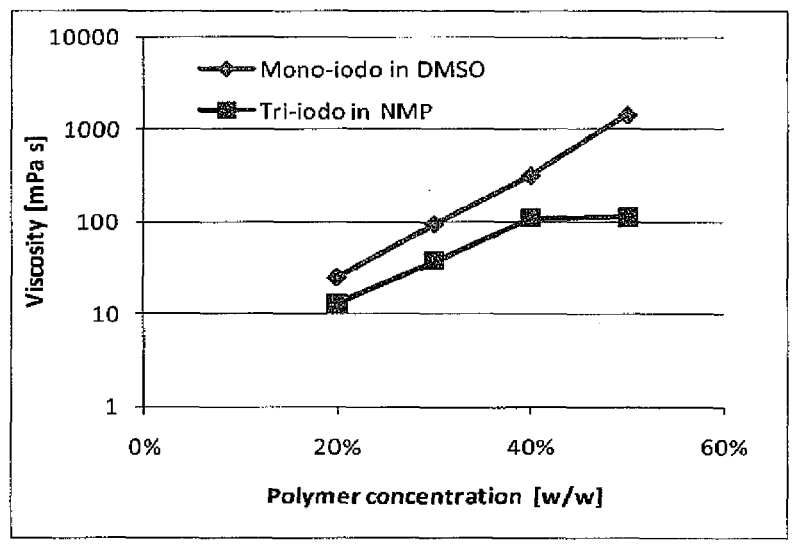
FIG. 5 represents a graph showing the change of viscosity [mPa·s] of two solutions containing a iodo-benzylether-PVA of the present invention prepared from PVA 13 kDa in relation to a change of the concentration (% w/w) of the iodo-benzylether-PVA in solution.

FIG. 5 shows the increase of the viscosity when the concentration of the iodo-benzylether-PVA obtained from PVA 13 kDa in the specified solvent increases.

Therefore, FIG. 5 shows that the viscosity of the embolizing compositions can be tailored by iodo-benzylether-PVA concentration, iodo-benzylether-PVA type, and solvent nature to obtain the high viscosity (ca 500 mPa·s) required for aneurysm embolization as well as the lower viscosity (ca 50 mPa·s) adequate for embolization of small capillaries.

For comparison, the Onyx™ 34 commercial embolizing composition has a viscosity of 55 mPa·s.

Example 5

Radiopacity of Embolizing Compositions

Solutions of MIB-PVA 13 kDa obtained in Example 2 and TIB-PVA 13 kDa obtained in Example 1 at a concentration of 33% w/w in NMP were poured in radiolucent 1 ml Eppendorfs. X-ray absorption was measured on a computerized tomograph scan (CT-scan, Skyscan 1076, Skyscan, Belgium) using a 0.5 mm aluminum window, under 50 kV and 200 μA. 180 degrees tomograms were acquired and reconstructed (Nrecon 1.5.1.4, Skyscan, Belgium), and pixel gray level was averaged over the whole embolic image (imageJ program, NIH). For calibration in Hounsfied units (HU), water (HU=0) and air (HU=−1000) were used.

Figure 6:
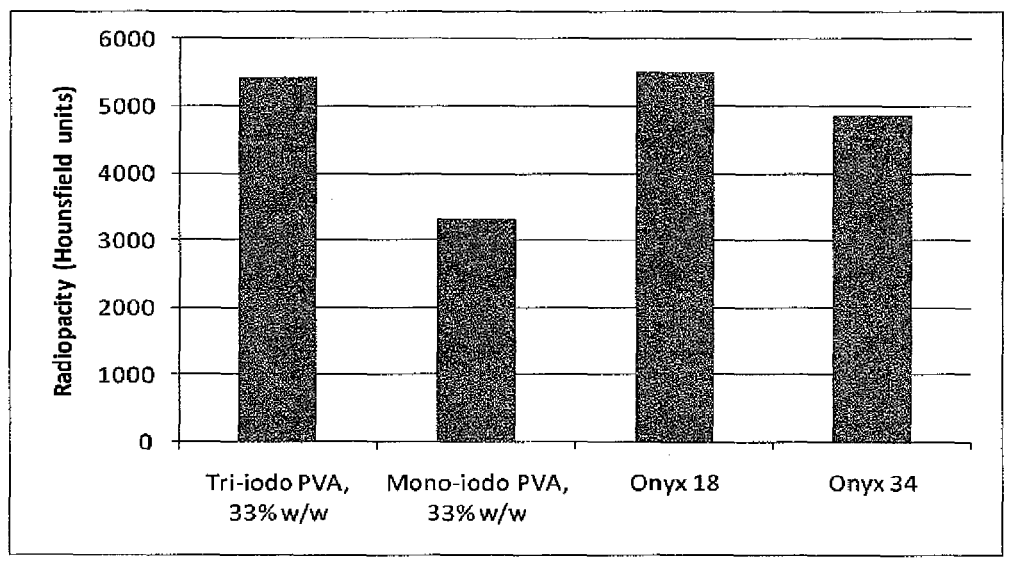
FIG. 6 represents a graph illustrating the radiopacity of two injectable embolizing compositions of the present invention, as compared with the radiopacity of Onyx™ 18 and Onyx™ 34.

As shown in FIG. 6, the radiopacity of the composition containing 33% w/w of TIB-PVA 13 kDa of Example 1 in NMP is comparable to that of commercial liquid embolizing compositions (Onyx™ 34 and Onyx™ 18) containing 20% of radiopaque tantalum.

However, the embolizing composition containing 33% w/w of MIB-PVA 13 kDa of Example 2 in NMP shows lower radiopacity, as expected from its lower iodine content.

Noteworthy, if left at rest for more than a few minutes, tantalum in Onyx™ sedimented, leading to highly inhomogeneous radiopacity.

From these data, it is expected that a compositions containing 55% w/w of 4-monoiodobenzyl ether of poly(vinyl alcohol) in NMP would have a radiopacity comparable to the Onyx™ compositions.

Example 6

Embolization of a Model Aneurysm

Two injectable embolizing compositions of the present invention and Onyx™ 34 commercial composition were tested for their ability to fill an aneurysm model. We used as a model a 10 mm-diameter sphere affixed to a glass tube. The model was flushed with saline using a rotary pump under a 30 cm/s flow speed mimicking blood flow. The injectable embolizing composition was injected into the aneurysm model with a 22 G needle.

Figure 7A:
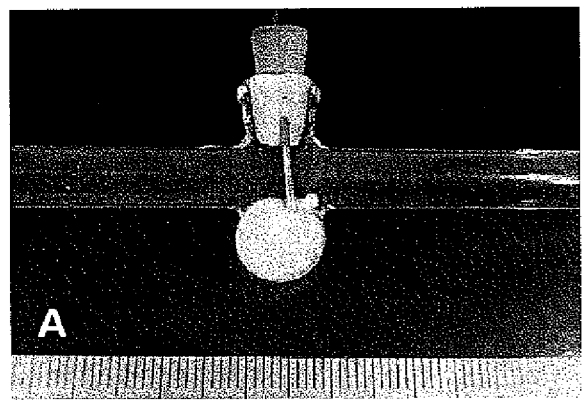
FIG. 7a is a photograph showing embolization of an aneurysm model with an injectable embolizing composition of the present invention containing 33% w/w of 2,3,5-triiodobenzylether of poly(vinyl alcohol) dissolved in NMP.

FIG. 7a shows embolization of an aneurysm model with an injectable embolizing composition (A) of the present invention containing 33% w/w of TIB-PVA 13 kDa obtained in Example 1 in NMP.

Figure 7B:
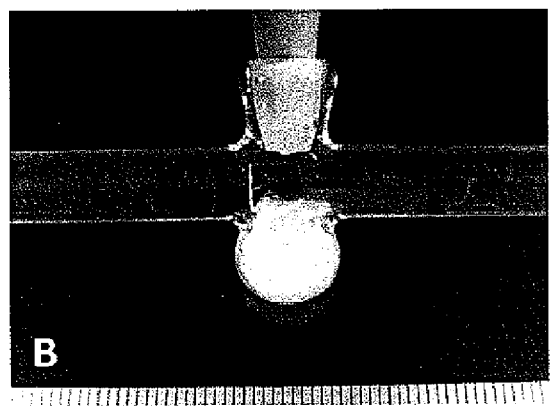
FIG. 7b is a photograph showing embolization of an aneurysm model with an injectable embolizing composition of the present invention containing 33% w/w of 4-iodobenzylether of poly(vinyl alcohol) dissolved in NMP.

FIG. 7b shows embolization of a aneurysm model with an injectable embolizing composition (B) of the present invention containing 33% w/w of MIB-PVA 13 kDa obtained in Example 2 in NMP.

Figure 7C:
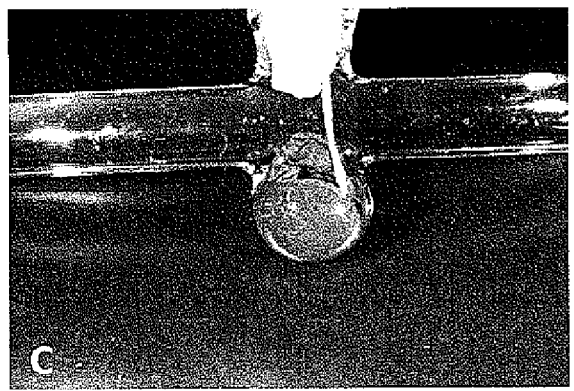
FIG. 7c is a photograph showing embolization of an aneurysm model with Onyx™ 34 commercial embolizing composition.

FIG. 7c shows embolization of an aneurysm model with Onyx™ 34 commercial embolizing composition.

These FIGS. 7a, 7b and 7c clearly illustrate the ability of the intrinsically radiopaque injectable embolizing compositions (A, B) to fill completely the sphere with a compact mass, in a manner comparable to the commercially available injectable embolizing composition Onyx™ 34. (C).

For all injectable embolizing compositions A, B and C, a cohesive mass was formed under flow within 3 minutes.

Example 7

Synthesis of 2,3,5-tri-iodobenzylether-PVA from PVA 13 kDa (TIB-PVA 13 kDa)

447 mg of PVA 13 kDa (9 mmol, 1 eq) was dissolved in 30 ml of dry NMP (concentration of PVA: 0.3M) under nitrogen gas flow. The reaction mixture was stirred for 5 minutes at 130° C.; then the temperature was decreased to 50° C. 727 mg of ground and dried NaOH (18 mmol, 2 eq) was added and the mixture was stirred for 10 minutes. Then, 5 g of 2,3,5-triiodobenzyl bromide (9 mmol, 1 eq) was added. After 30 minutes, the mixture was cooled to room temperature and 30 ml of cold water was added under stirring. A solid precipitate appeared, was filtered and washed with methanol. After conventional steps of purification, 800 mg of TIB-PVA 13 kDa including 26% of residual NMP was obtained (representing 208 mg of NMP and 592 mg of TIB-PVA 13 kDa).

$^1$H-NMR (DMSO-d6): 1.35-1.76 ppm (m, 3.74 au, CH$_2$ PVA chain (2(x+y)), 1.9 ppm (q, 4.65 au, CH$_2$)*, 2.1 ppm (t, 3.82 au, CH$_2$)*, 2.6 ppm (s, 5.63 au, CH$_3$)* 3.6-4.0 ppm (m, 1.79 au, CH PVA chain (x+y)), 4.1-4.6 ppm (m, 2.71 au, CH$_2$ benzyl and residual OH (2x+y)), 7.6 ppm (s, 1.04 au, H aromatic (x)), 8.06 ppm (s, 1.0 au, H aromatic (x))
*Residual NMP The DS calculated from the NMR lines according to the method of Example 1 was 53%.

Example 8

Synthesis of 2,3,5-tri-iodobenzylether-PVA from PVA 47 kDa (TIB-PVA 47 kDa)

The same synthesis method as in Example 7 was used in order to graft the 2,3,5-triiodobenzyl bromide with the PVA 47 kDa. After conventional steps of purification, TIB-PVA 47 kDa including residual NMP was obtained.

$^1$H NMR (DMSO-d6): 1.35-1.76 ppm (m, 3.42 au, CH$_2$ PVA chain (2(x+y)), 2.1 ppm (t, 3.07 au, CH$_2$)*, 3.6-4.0 ppm (m, 1.81 au, CH PVA chain (x+y)), 4.1-4.6 ppm (m, 2.72 au, CH$_2$ benzyl and residual OH (2x+y)), 7.59 ppm (s, 1.0 au, H aromatic (x)), 8.04 ppm (s, 1.0 au, H aromatic (x))
*Residual NMP The DS calculated from the NMR lines according to the method of Example 1 was 58%.

Example 9

Synthesis of 2,3,5-tri-iodobenzylether-PVA from PVA 61 kDa (TIB-PVA 61 kDa)

The same synthesis method as in Example 7 was used in order to graft the 2,3,5-triiodobenzyl bromide with the PVA 61 kDa PVA. After conventional steps of purification, TIB-PVA 61 kDa including residual NMP was obtained.

$^1$H NMR (DMSO-d6): 1.35-1.76 ppm (m, 4.33 au, CH$_2$ PVA chain (2(x+y)), 2.1 ppm (t, 6.36 au, CH$_2$)*, 3.6-4.0 ppm (m, 2.23 au, CH PVA chain (x+y)), 4.1-4.6 ppm (m, 2.97 au, CH$_2$ benzyl and residual OH (2x+y)), 7.59 ppm (s, 1.0 au, H aromatic (x)), 8.05 ppm (s, 1.0 au, H aromatic (x))
*Residual NMP The DS calculated from the NMR lines according to the method of Example 1 was 46%.

Example 10

Synthesis of 4-mono-iodobenzylether-PVA from PVA 13 kDa (MIB-PVA 13 kDa)

825 mg of PVA 13 kDa was dissolved in 55 ml of dry NMP under a nitrogen flow at 130° C. Then the temperature was decreased to 50° C. and 5 g of 4-monoiodobenzyl bromide was added. After 10 minutes, 1.35 g of dried sodium hydroxide was added. After 5 hours of reaction time, cold water was added and a paste material has appeared. The sticky paste could not be filtrated. Water was easily removed because the material was struck to the walls of the flask. After water was poured out, the pasty residue was washed with methanol and dried. After conventional steps of purification, MIB-PVA 13 kDa including residual NMP was obtained.

$^1$H-NMR (DMSO-d6): 1.35-1.76 ppm (m, 2.9 au, CH$_2$ PVA chain (2(x+y)), 1.9 ppm (q, 1.02 au, CH$_2$)*, 2.1 ppm (t, 1 au, CH$_2$)*, 2.7 ppm (s, 1.5 au, CH$_3$)*, 3.6-3.79 ppm (m, 1.6 au, CH PVA chain (x+y)), 4.38-4.48 ppm (m, 2.6 au, CH$_2$ benzyl and residual OH (2x+y)), 7.03 ppm (s, 2.0 au, H aromatic (2x)), 7.55 ppm (s, 2.0 au, H aromatic (2x))
*Residual NMP The DS calculated from the NMR lines according to the method of Example 2 was 69%.

Example 11

Synthesis of 4-mono-iodobenzylether-PVA from PVA 47 kDa (MIB-PVA 47 kDa)

The same synthesis method as in Example 10 was used in order to graft the 4-monoiodobenzyl bromide with the PVA 47 kDa. After conventional steps of purification, MIB-PVA 47 kDa including residual NMP was obtained.

$^1$H NMR (DMSO-d6): 1.35-1.76 ppm (m, 4.1 au, CH$_2$ PVA chain (2(x+y)), 1.9 ppm (q, 0.9 au, CH$_2$)*, 2.1 ppm (t, 0.9 au, CH$_2$)*, 2.7 ppm (s, 1.3 au, CH$_3$)*, 3.3 ppm (t, 0.98 au, CH$_2$)*, 3.6-3.79 ppm (m, 1.9 au, CH PVA chain (x+y)), 4.38-4.48 ppm (m, 2.9 au, CH$_2$ benzyl and residual OH (2x+y)), 7.03 ppm (s, 2.0 au, H aromatic (2x)), 7.55 ppm (s, 2.0 au, H aromatic (2x))

*Residual NMP

The DS calculated from the NMR lines according to the method of Example 2 was 49%.

Example 12

Synthesis of 4-mono-iodobenzylether-PVA from PVA 61 kDa (MIB-PVA 61 kDa)

The same synthesis method as in Example 10 was used in order to graft the 4-monoiodobenzyl bromide with the PVA 61 kDa. After conventional steps of purification, MIB-PVA 61 kDa including residual NMP was obtained.

$^1$H-NMR (DMSO-d6): 1.35-1.76 ppm (m, 3.9 au, CH$_2$ PVA chain (2(x+y)), 1.9 ppm (q, 2.4 au, CH$_2$)*, 2.1 ppm (t, 2.2 au, CH$_2$)*, 2.7 ppm (s, 3.3 au, CH$_3$)*, 3.6-3.79 ppm (m, 1.4 au, CH PVA chain (x+y)), 4.38-4.48 ppm (m, 2.7 au, CH$_2$ benzyl and residual OH (2x+y)), TOO ppm (s, 1.9 au, H aromatic (2x)), 7.54 ppm (s, 2.0 au, H aromatic (2x))

*Residual NMP

The DS calculated from the NMR lines according to the method of Example 2 was 51%.

Example 13

Grafting 4-monoiodobenzyl bromide and 2,3,5-triiodobenzyl bromide on PVA 47 kDa to prepare the polymer with mixed grafted units (4-monoiodobenzyl-ether)(2,3,5-triiodobenzylether)-PVA 47 kDa (MTIB-PVA 47 kDa)

The synthesis was carried out in a flame-dried 3-necked flask and under N$_2$-atmosphere. Poly(vinyl alcohol) (MW=47000, 80 mmol of monomer-units, 3.52 g) was placed in the reaction flask which was then N$_2$-vacuum purged twice. Anhydrous NMP (280 mL) was transferred from a sealed bottle to the reaction flask using a canula. The mixture was stirred for 30 minutes at 130° C. in order to dissolve all of the polymer. The mixture was subsequently cooled and stirred at 50° C. NaOH (2 eq., 160 mmol, 6.4 g), which was freshly ground from pellets into a fine powder, was added in one go. The mixture was stirred at 50° C. for 30 minutes, resulting in a colour change of the solution from yellow to brown. A mixture of 4-iodobenzyl bromide (0.5 eq., 40 mmol, 11.9 g) and 2,3,5-triiodobenzyl bromide (0.5 eq., 40 mmol, 22.0 g), obtained by mixing the two solids in a beaker with a spatula, were added as a powder in one go. This resulted in a rapid colour change from brown back to yellow. The mixture was stirred for 1 hour. After cooling to room temperature, the polymer was precipitated by adding the solution dropwise to a well-stirred volume of demi-water (2.8 L), which resulted in the dissolution of white solid flakes. The mixture was then filtered over a P1-glassfilter, the white crude material was washed with another 500 mL demi-water and subsequently twice with 500 mL acetone. The crude product was dried over night under vacuum, and redissolved in THF (200 mL). The polymer was then purified via precipitation using toluene as non-solvent. Transferring the THF-solution dropwise to a well-stirred volume of toluene (2 L) yielded white milky mixture, which was filtered over a P4-glassfilter. The white solid material was then washed with 500 mL acetone and dried over night under vacuum (~10$^{-2}$ mbar) at 100° C., providing 11.5 g of the product as a light-brown solid material.

Figure 8:
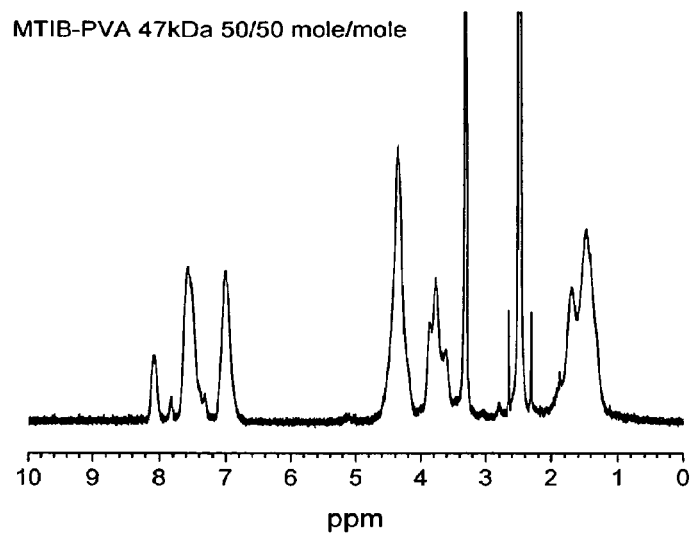
FIG. 8 shows the $^1$H-NMR spectrum of MTIB-PVA 47 kDa of the present invention prepared according to Example 13.

The DS is calculated from the $^1$H-NMR spectrum recorded in DMSO-d6 containing a small quantity of water represented in FIG. 8. The following broad signals with chemical shifts of the maxima of the signals are identified:

| | | | |
|---|---|---|---|
| 1. | $S_1$ | δ 8.0-8.1 ppm | CH (TIB-Phenyl, para position) |
| 2. | $S_2$ | δ 7.5-7.6 ppm | CH (TIB-Phenyl, ortho position) |
| 3. | $S_2$ | δ 7.5-7.6 ppm | 2 × CH (MIB-Phenyl, meta position) |
| 4. | $S_3$ | δ 6.9-7.0 ppm | 2 × CH (MIB-Phenyl, ortho position) |
| 5. | $S_4$ | δ 4.3-4.4 ppm | CH$_2$ (TIB-Benzyl) |
| 6. | $S_4$ | δ 4.3-4.4 ppm | CH$_2$ (MIB-Benzyl) |
| 7. | $S_4$ | δ 4.3-4.4 ppm | OH (Backbone PVA) |
| 8. | $S_5$ | δ 3.7-3.8 ppm | CH (Backbone PVA) |
| 9. | $S_6$ | δ 3.3-3.4 ppm | H$_2$O (Trace water) |
| 10. | $S_7$ | δ 2.4-2.5 ppm | CHD$_2$ (DMSO-d6) |
| 11. | $S_8$ | δ 1.4-2.6 ppm | CH$_2$ (Backbone PVA) |

The degrees of substitution (DS) for MIB and TIB separately ($DS_{MIB}$ and $DS_{TIB}$, respectively) are calculated as:

$$DS_{MIB} = S_3/S_8$$

$$DS_{TIB} = 2S_1/S_8$$

The overall degree of substitution is $DS = DS_{MIB} + DS_{TIB}$

The DS calculated from NMR data are $DS_{MIB} = 0.3$ (30%) and $DS_{TIB} = 0.3$ (30%).

The % I is given by $$\%I = \frac{DS \times M_{iodine} \times (n_1 \times p + n_2 \times (1-p))}{M_{non-grafted} \times (1-DS) + (M_{grafted-1} \times p + xM_{grafted-2}(1-p)) \times DS} \times 100$$

wherein $n_1$: number of Iodine atoms on aromatic ring of iodobenzyl unit #1

$n_2$: number of Iodine atoms on aromatic ring of iodobenzyl unit #2

$M_{grafted-1}$ molar mass of iodobenzyl unit #1

$M_{grafted-2}$ molar mass of iodobenzyl unit #2 p mole fraction of iodobenzyl unit #1; $p = DS_1/(DS_1 + DS_2)$

The DS calculated from the NMR lines of MTIB-47 kDa PVA was 60%

The % I calculated from the DS of MTIB-47 kDa PVA was 62%.

Example 14

Embolization Capability of Various Radiopaque Polymer or Blend of Polymers Formulations According to the Present Invention Using a Hydrogel Model Embolization formulations of the present invention based on solution of 4-mono-iodobenzyl-PVA (MIB) and 2,3,5-tri-iodobenzyl-PVA (TIB) were synthesized from PVA of various molar masses (13,000-23,000, 47,000, 61,000 and 125,000 g/mol abbreviated 13 kDa PVA, 47 kDa PVA, 61 kDa PVA and 125 kDa PVA).

The solutions were made by dissolving each of the polymers in NMP at 33% w/w final concentration (otherwise mentioned).

In addition, mixtures of MIB-PVA 47 kDa and TIB-PVA 47 kDa in various ratio (MIB-PVA:TIB-PVA 25:75, 40:60, 50:50, 60:40, 75:25 in weight %) were also evaluated.

Degrees of substitution (DS) of the iodo-benzylether-PVA of the present invention used in this Example were 53% for MIB-PVA 47 kDa, 58% for TIB-PVA 47 kDa, 67% for MIB-PVA 61 kDa, 58% for the TIB-PVA 61 kDa and 61% for the TIB-PVA 125 kDa.

Heating at 90° C. was used to accelerate dissolution. The liquid embolizing formulations were tested in a hydrogel model made of polyvinyl alcohol (see FIGS. 9a and 9b). A 3 mm-diameter hole in the hydrogel was fed with saline flow (10 mL/min) using a pump to mimic capillary blood flow. A catheter was inserted and a flow diverter limited pressure buildup upon embolization.

Upon injection of ca 0.1 mL of each embolic, cylinder-shaped polymer plugs could be formed, resulting in capillary obstruction.

Figure 9A:
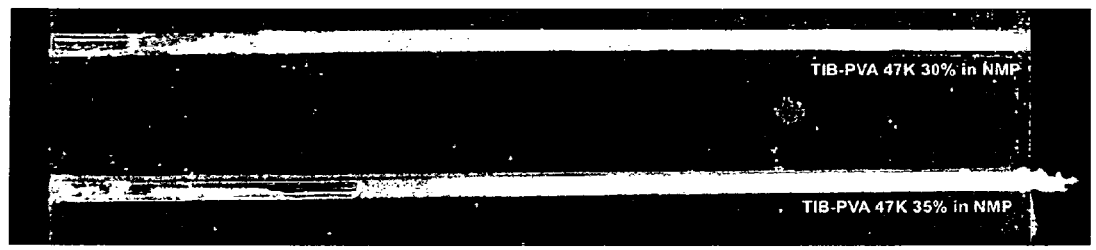
FIGS. 9a et 9b are photographic (FIG. 9a) and fluoroscopic x-ray (FIG. 9b) images of plugs obstructing hydrogel model obtained from an injectable embolizing formulation of the present invention at two concentrations of 30% and 35% w/w in NMP of 2,3,5-tri-iodobenzylether-PVA 47 kDa (DS=58%) as reported in Example 14, wherein saline flows from the right to the left.
Figure 9B:
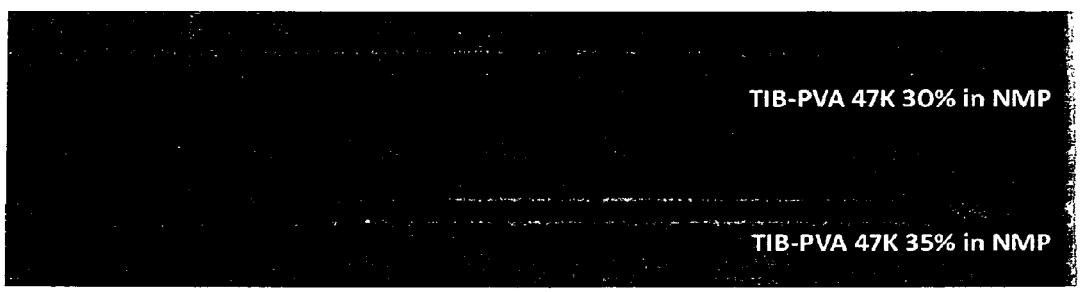
Figure 10:
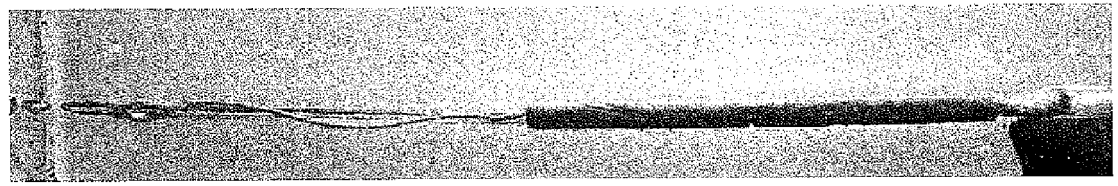
FIG. 10 is a photograph showing a plug obtained following injection into hydrogel model of a mixture of 4-mono-iodobenzylether-PVA 61 kDa (DS=67%) and 2,3,5-tri-iodobenzylether-PVA 61 kDa (DS=58%) in 50:50 wt % at a total concentration of 33 wt % in NMP as reported in Example 14, wherein saline flows from the right to the left.

FIGS. 9a and 9b show the typical plugs obtained with the formulation of the present invention containing TIB-PVA 47 kDa at concentrations of 30% and 35% in NMP.

The highest polymer concentration did show slightly better embolization ability in this specific setting, as well as an increased radiopacity.

In case of backward reflux, stopping the injection for 1 to 3 min generally allowed to continue the embolization distally.

The catheters could generally be withdrawn easily, the MIB-PVA and TIB-PVA of the present invention demonstrating little adhesion to the catheters.

The TIB-PVA 47 kDa, TIB-PVA 61 kDa and TIB-PVA 125 kDa could embolize the hydrogel capillary model in a similar manner, although the low molar mass polymer, which demonstrates the lower solution viscosity, may be preferred for the embolization of small vascular structures. MIB-PVA 47 kDa and MIB-PVA 61 kDa could similarly embolize the hydrogel capillary, although showing a slower precipitation than the TIB-PVA.

Mixtures of MIB-PVA and TIB-PVA at various ratios were also able to obstruct totally the capillary following their precipitation.

An increasingly faster precipitation was observed with increasing TIB-PVA contents, as well as harder but more brittle precipitated cast.

These results indicates that a whole family of formulations can be obtained using MIB-PVA and TIB-PVA, tailoring their properties by adapting polymer molar mass, concentration and MIB-PVA/TIB-PVA ratio.

Example 15

Embolization Capability of PVA Polymers Grafted with Mixed Mono-Iodo and Tri-Iodobenzyl Groups A MTIB-PVA 47 kDa was obtained from Example 13 using equal molar ratio of 4-mono-iodobenzyl bromide and 2,3,5-triiodobenzyl bromide for the synthesis, corresponding to a MIB:TIB 38:62 wt % ratio. PVA 47 kDa starting material could be substituted to DS=60%. A liquid embolic formulation was made by dissolving the MTIB-PVA 47 kDa in NMP at 33% w/w final concentration. Heating at 90° C. was used to accelerate dissolution. The liquid formulations were tested in a hydrogel model made of polyvinyl alcohol as show in the previous Example 14. Upon injection of ca 0.1 mL, the polymer solution in NMP could embolize the lumen of the hydrogel capillary. Polymer plugs could be formed, provoking obstruction and flow arrest. The catheter could be withdrawn easily. These results points out that a whole family of formulations can be obtained using MTIB-PVA polymers, tailoring their properties by adapting polymer molar mass, concentration and molar ratio of 4-mono-iodobenzyl bromide and 2,3,5-triiodobenzyl bromide.

Example 16

Figure 11A:
FIG. 11a is a photograph showing a viscous injectable embolizing formulation of the present invention containing 4-mono-iodobenzylether-PVA 47 kDa (DS=56%) at a concentration of 33 wt % in NMP loaded with superparamagnetic iron nanoparticles at a concentration of 20% w/V, as reported in Example 16.
Figure 11B:
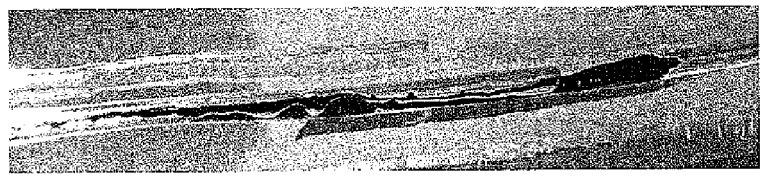
FIG. 11b is a photograph showing a hyperthermic semi-solid smooth implant formed after injection of the viscous injectable embolizing formulation of the present invention shown in FIG. 11a into hydrogel model, as reported in Example 16.

In Situ Forming Embolizing Compositions Added with SPIONs-Containing Silica Beads for Controlled, Local Hyperthermia A solution of MIB-PVA 47 kDa having a DS of 56% was dissolved at 33% w/w in NMP. Silica beads loaded with superparamagnetic iron oxide nanoparticles (Degussa Mag-Silica 50-80) were added to this solution at a concentration of 20% w/V. The viscous liquid obtained could be injected through a 21 G needle, forming a semi-solid, smooth and brown polymer ball within 3 min (see FIGS. 11a and 11b). Injection in a hydrogel model of a 3-mm diameter straight vessel (similarly to Example 14) demonstrated the ability of this formulation to stop the 10 ml/min flow, mimicking the embolization of a natural vessel.

The paste was precipitated into small cylinders, 6 mm diameter. This implant was inserted into an adiabatic calorimeter at room temperature and submitted to an alternating magnetic field of 9 mT, 141 kHz (Huttinger TIG-2.5/300) during five minutes. The temperature recorded by optical probes showed a fast increase leveling to a plateau temperature increase of DT=+16.6° C. as shown in FIG. 12. The fast increase with a slope of 16° C./min corresponds to a power dissipation of 5.1 W/g of iron oxide. Such a temperature increase is expected to lead in vivo to thermoablation of surrounding tissues.

Example 17

Figure 13:
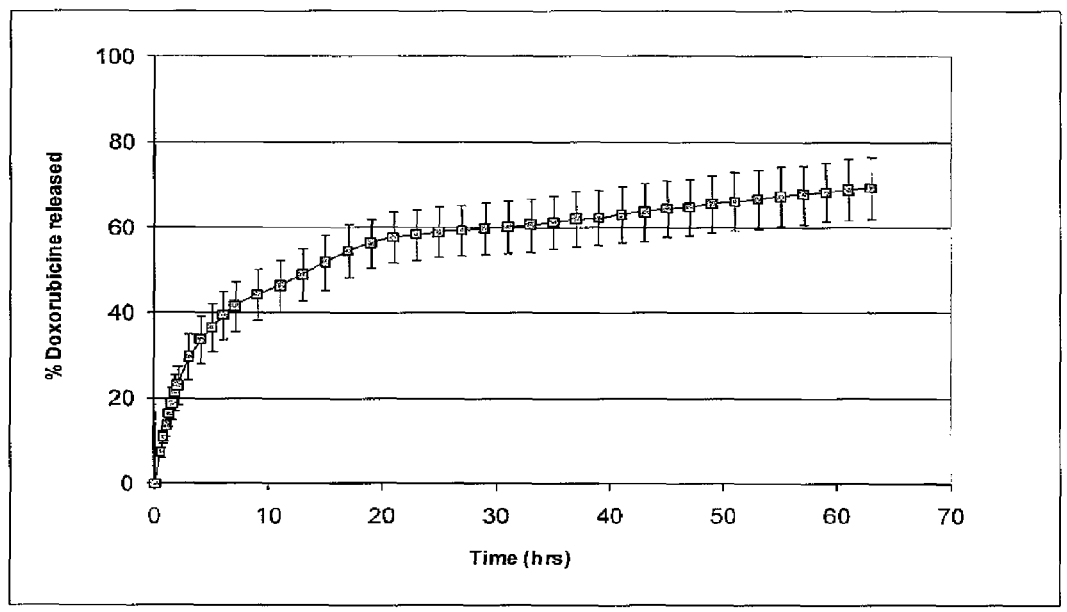
FIG. 13 represents a graph illustrating doxorubicine released from a radiopaque plug (n=3, error bars indicate standard error of the mean (semi)) in saline medium, formed from an injectable embolizing formulation of the present invention as reported in Example 17.

Loading and Release of an Anticancer Agent from a Precipitated Radiopaque Polymer Mass Doxorubicine hydrochloride was dissolved in N-methyl pyrrolidone (NMP, at 25 mg/mL). TIB-PVA 47 kDa having a DS of 58% was added at 33% w/w final concentration. The solution was injected into cylindrical alginate molds to produce 6-mm diameter plugs (ca 0.3 g each). The doxorubicine-loaded samples were incubated in 100 mL saline at 37° C. under agitation. Doxorubicine was quantified by measurements of the optical absorption of the supernatant at 479 nm wavelength. FIG. 13 shows the obtained gradual release of the anticancer agents over 3 days.

Example 18

Coating of Medical Devices with Radiopaque Polymer Solution

A radiopaque coating was deposited onto a catheter tip by dipping and solvent evaporation. Briefly, TBI-PVA 47 kDa having a DS of 58% were dissolved in NMP at 40° C. at a final concentration of 33% w/w. The tip of a catheter (Cordis Envoy GC) was dipped for 5 s into the radiopaque polymer solution, withdrawn and dried at room temperature, keeping the catheter under axial rotation to obtain an even coating. The tip coated with TIB-PVA 47 kDa is illustrated in FIGS. 14a and 14b. Radiopaque and catheter polymers were bound together by virtue of solvent evaporation. Other solvents were assessed, such as DMSO, leading to similar radiopaque coatings.

Example 19

Fabrication of Nanoparticles from Radiopaque Iodo-Benzylether of the Present Invention by Nanoprecipitation Radiopaque nanoparticles were prepared by the nanoprecipitation method as follows: 100 mg of MIB-PVA 47 kDa having a DS of 49% was dissolved in THF (20 ml) at room temperature to form the diffusing phase. The diffusing phase was then added by means of a syringe to the dispersing phase constituted of phosphate buffered saline (PBS, 40 ml) containing 0.25% surfactant Pluronic' F68 under stirring. The aqueous phase turned milky as the organic phase was poured, leading to a homogeneous milky dispersion at the end. THF was evaporated under reduced pressure. The mean diameter of the nanoparticles, as measured using a Malvern NanoZS instrument, was 170 nm, with a monomodal distribution.

The same method was used to produce particles with TIB-PVA 13 kDa having a DS of 53%.

The following Table, showing the TIB-PVA 13 kDa nanoparticle diameter as a function of the concentration of TIB-PVA 13 kDa in the diffusing phase or the concentration of Pluronic F68 in PBS, further demonstrates that nanoparticle diameter could be tailored by varying the concentration of TIB-PVA in the diffusing phase or the concentration of Pluronic F68 in PBS. Smaller particles, in the 50-90 nm diameter range, could be obtained by using pure water instead of PBS.

| Concentration TIB-PVA - Pluronic ® | Diameter of nanoparticles (nm) |
|---|---|
| 0.1%-0.5% | 300 |
| 0.5%-0.5% | 170 |
| 0.25%-0.25% | 240 |
| 0.25%-0.5% | 176 |
| 1%-0.75% | 113 |
| 1%-0.1% | 108 |

Example 20

Comparative Degradation of Radiopaque Iodo-Benzylether-PVA (Ether) Versus Radiopaque Iodobenzoate-PVA (Ester) Nanoparticles 1. Degradation of MIB-PVA 47 kDa-Based Nanoparticles Polymer degradation was monitored through the absorbance of the expected degradation product, 4-monoiodobenzoic acid. Polymer nanoparticles were used for their high specific area. For comparison with ethers, esters of radiopaque polymers were prepared in Preparations Examples 5 and 6 (Elaboration of radiopaque iodinated nanoparticles for in situ control of local drug delivery. D. Mawad, H. Mouaziz, A. Penciu, H. Méhier, B. Fenet, H. Fessi, Y. Chevalier; *Biomaterials* 2009, 30, 5667-5674). Nanoparticles of MIB-PVA 47 kDa prepared in Example 11 and MIB/Ester-PVA 13 kDa prepared in Preparation Example 6 (DS=49% and 40%, respectively) were then produced by nanoprecipitation in PBS as described in the Example 19, both with a mean diameter of ca. 170 nm.

Figure 15:
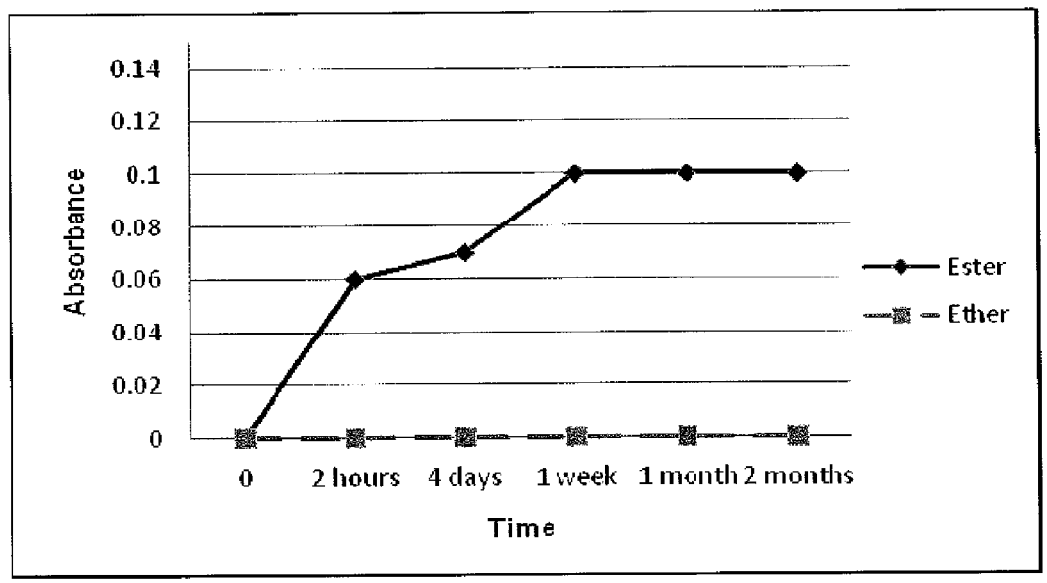
FIG. 15 represents a graph illustrating the evolution of the absorbance of nanoparticle degradation products for the 4-mono-iodobenzylether-PVA 47 kDa and 4-mono-iodobenzoate-PVA 47 kDa as reported in Example 20.1.

In order to study the released degradation products, the nanoparticles suspensions were incubated at 37° C. in phosphate-buffered saline (PBS). At given time points, the nanoparticles were collected by centrifugation and the supernatants of centrifuged suspensions were analyzed by UV absorbance at 250 nm wavelength—the absorbance maxima of 4-monoiodobenzoic acid. FIG. 15 displays the time-evolution of the absorbance, reflecting the release of degradation products. Whereas no measurable release was observed with the ether-based nanoparticles after two months, a clear increase was rapidly observed for the ester-bases nanoparticles, showing a fast degradation of the ester-based polymer. These results indicated that the ether-based nanoparticles are stable in PBS even after one month, whereas the ester-based nanoparticles are not.

2. Degradation of TIB-PVA 13 kDa-Based Nanoparticles

Figure 16:
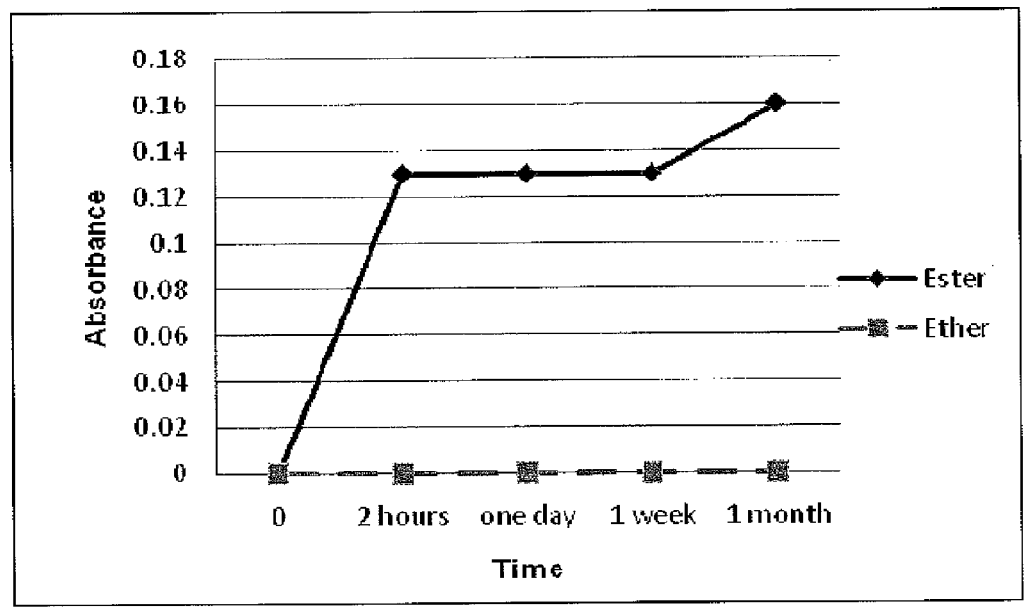
FIG. 16 represents a graph illustrating the evolution of the absorbance of nanoparticle degradation products for the 2,3,5-tri-iodobenzylether-PVA 13 kDa and 2,3,5-tri-iodobenzoate-PVA 13 kDa as reported in Example 20.2.

Nanoparticle degradation testing was repeated using the same methods, with TIB-PVA 13 kDa obtained in Example 7 and TIB/Ester-13 kDa obtained in Preparation Example 5 (DS=53% and 34%, respectively). Nanoparticles of ca. 170 nm diameter were produced in PBS for both polymers. The absorbance wavelength was fixed at 229 nm, corresponding to the peak absorption of the expected degradation product, 2,3,5-tri-iodobenzoic acid. As described on the FIG. 16, the absorbance of the ester supernatant increased slowly until 0.16 after one month, corresponding to the release of 8% of the iodinated groups. No measurable release was observed with the ether polymer. These results indicate that the ether-based nanoparticles ether are stable in PBS even after one month, whereas the ester-based nanoparticles are not.

The invention claimed is:

1. A method of embolizing an area of treatment comprising:
   providing a composition that includes a radiopaque, non-biodegradable, water-insoluble iodinated benzyl ether of poly(vinyl alcohol) consisting of a poly(vinyl alcohol) (PVA) having covalently grafted thereon iodinated benzyl groups comprising from 1 to 4 iodine atoms per benzyl group as the only substituents wherein a grafted repeating unit has formula (I)

wherein n is from 1 to 4; and
   introducing the composition into the area of treatment.

2. The method of claim 1, wherein the composition further comprises a water-miscible, biocompatible solvent and the concentration of the radiopaque, non-biodegradable, water-insoluble iodinated benzyl ether of poly(vinyl alcohol) is in the range of about 5 wt % to about 65 wt %.

3. The method of claim 2, wherein the water-miscible biocompatible solvent is selected from the group consisting of dimethylsulfoxide, N-methylpyrrolidone, glycofurol, pyrrolidone, ethanol, propylene glycol, polyethylene glycol, 2,2-dimethyl-1,3-dioxolane-4-methanol, glycerol formal, tetrahydrofurfuryl alcohol, dimethyl isosorbide, ethyl lactate, hydroxyethyllactamide, N,N-dimethylacetamide, and mixtures thereof.

4. The method of claim 1 wherein the area of treatment includes a blood vessel.

5. The method of claim 2 wherein the area of treatment is selected from one of a blood vessel and a tumor.

6. The method of claim 2, wherein the composition further comprises superparamagnetic iron oxide nanoparticles (SPIONs).

7. The method of claim 2, wherein the composition further comprises an anticancer agent.

8. The method of claim 2 wherein the water-miscible biocompatible solvent is selected from the group consisting of, dimethylsulfoxide (DMSO), N-methylpyrrolidone (NMP), glycofurol, and mixtures thereof.

9. A method of embolizing a tumor comprising:
providing a composition that includes a radiopaque, non-biodegradable, water-insoluble iodinated benzyl ether of poly(vinyl alcohol) consisting of a poly(vinyl alcohol) (PVA) having covalently grafted thereon iodinated benzyl groups comprising from 1 to 4 iodine atoms per benzyl group as the only substituents wherein a grafted repeating unit has formula (I)

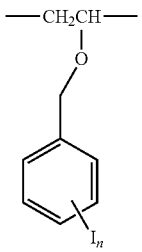

wherein n is from 1 to 4; and
introducing the composition into a tumor so that the composition forms in-situ a cohesive mass in the tumor.

10. The method of claim 9, wherein the composition further comprises a water-miscible, biocompatible solvent and the concentration of the radiopaque, non-biodegradable, water-insoluble iodinated benzyl ether of poly(vinyl alcohol) is in the range of about 5 wt % to about 65 wt %.

11. The method of claim 10, wherein the water-miscible biocompatible solvent is selected from the group consisting of dimethylsulfoxide, N-methylpyrrolidone, glycofurol, pyrrolidone, ethanol, propylene glycol, polyethylene glycol, 2,2-dimethyl-1,3-dioxolane-4-methanol, glycerol formal, tetrahydrofurfuryl alcohol, dimethyl isosorbide, ethyl lactate, hydroxyethyllactamide, N,N-dimethylacetamide, and mixtures thereof.

12. The method of claim 9, wherein the composition further comprises superparamagnetic iron oxide nanoparticles (SPIONs) so that the composition forms in-situ a hyperthermic solid or semi-solid implant for treating the tumor by hyperthermia.

13. The method of claim 9, wherein the composition further comprises an anticancer agent.

14. The method of claim 10, wherein the water-miscible biocompatible solvent is selected from the group consisting of dimethylsulfoxide (DMSO), N-methylpyrrolidone (NMP), glycofurol, and mixtures thereof.

* * * * *